US006575747B1

(12) United States Patent
Riitano et al.

(10) Patent No.: US 6,575,747 B1
(45) Date of Patent: *Jun. 10, 2003

(54) ENDODONTIC INSTRUMENTS ADAPTED TO PROVIDE VARIABLE WORKING LENGTHS AND RELATED METHODS FOR USING THE INSTRUMENTS

(75) Inventors: Francesco Riitano, Soverato (IT); Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/639,699

(22) Filed: Aug. 16, 2000

Related U.S. Application Data

(63) Continuation-in-part of application No. 09/425,849, filed on Oct. 22, 1999, now abandoned.

(51) Int. Cl.$^7$ ................................................ A61C 5/02
(52) U.S. Cl. ...................................... 433/102; 433/127
(58) Field of Search .......................... 433/102, 81, 127, 433/224

(56) References Cited

U.S. PATENT DOCUMENTS

| | | | | | |
|---|---|---|---|---|---|
| 3,578,745 | A | * | 5/1971 | Garnier | 433/102 |
| 3,772,791 | A | * | 11/1973 | Malmin | 433/224 |
| 4,295,827 | A | * | 10/1981 | Martin et al. | 433/81 |
| 4,484,891 | A | * | 11/1984 | Nash | 433/116 |
| 4,538,989 | A | * | 9/1985 | Apairo, Jr. et al. | 433/102 |
| 4,773,855 | A | * | 9/1988 | Levy | 433/102 |
| 4,840,566 | A | * | 6/1989 | Leonard | 433/102 |
| 4,904,185 | A | * | 2/1990 | McSpadden | 433/102 |
| 4,971,556 | A | * | 11/1990 | Ritano | 433/102 |
| 5,127,832 | A | * | 7/1992 | Zdarsky | 433/102 |
| 5,236,358 | A | * | 8/1993 | Sieffert | 433/119 |
| 5,350,298 | A | * | 9/1994 | Delaire | 433/81 |
| 5,498,158 | A | * | 3/1996 | Wong | 433/102 |
| 5,586,886 | A | * | 12/1996 | Roane | 433/224 |
| 5,735,690 | A | * | 4/1998 | Malentacca | 433/102 |
| 5,947,730 | A | * | 9/1999 | Kaldestad | 433/102 |

* cited by examiner

Primary Examiner—John J. Wilson
(74) Attorney, Agent, or Firm—Workman, Nydegger & Seeley

(57) ABSTRACT

A dental instrument is provided for use in an endodontic procedure which has a file extending from a handle configured to enable the working length of the handle to be varied. The handle of the instrument is adapted to be received in and to be releasably held by a chuck or collet of an endodontic handpiece head. Both the handles and chucks are adapted to enable the handles to be appropriately positioned in the chuck of a dental handpiece head at various positions to yield a desired working length and to then be secured. The rim around the chuck is preferably configured to act as a stop during use of the handpiece. The instrument is most useful when configured with incremental adjustment indicators, preferably in uniform increments, such that the working length can be determined by viewing the indicators.

37 Claims, 16 Drawing Sheets

ENDODONTIC INSTRUMENTS ADAPTED TO PROVIDE VARIABLE WORKING LENGTHS AND RELATED METHODS FOR USING THE INSTRUMENTS

RELATED APPLICATIONS

This application is a continuation-in-part of U.S. patent application Ser. No. 09/425,849 which was filed on Oct. 22, 1999, now abandoned and is entitled Systems for Incrementally Adjusting the Working Length of Endodontic Instruments. For purposes of disclosure of the present invention, Ser. No. 09/425,849 is incorporated herein by specific reference.

BACKGROUND OF THE INVENTION

1. The Field of the Invention

The present invention relates generally to dental instruments. More particularly, the present invention relates to an endodontic instrument for use in an endodontic procedure that has an adjustable working length.

2. The Relevant Technology

In order to preserve a tooth that has diseased pulp material therein, it is necessary to prevent bacterial proliferation within the pulp canal of the tooth by removing the diseased or necrotic pulp material from the pulp cavity or root canal. After the pulp material has been removed or extirpated from a tooth, the pulp cavity or root canal is typically filled or obturated with an inert material before being sealed off with an inert sealer of an aseptic material in order to prevent future infection of the tooth root. This procedure is referred to as root canal therapy.

During root canal therapy, it is essential that the entire root canal, including the root tip, be cleaned and filled to eliminate all organic matter contained within the root canal. The typical method followed for root canal therapy is to open the tooth to the pulp chamber and then work down to the root end Root canal cleaning or preparation is generally achieved by hand or mechanical instrumentation with files or bits that are configured to bore and/or cut. In order to gain access to the pulp chamber in a tooth, a hole is drilled through the tooth to the pulp chamber and subsequently widened. A variety of endodontic instruments are then used to enlarge and clean out the root canal to remove all the pulp tissue.

Conventional dental instruments used during root canal therapy such as various file instruments generally include a thin, flexible, metal shaft or file with an abrasive surface or sharp edges, which enables efficient cleaning of the root canal. A handle or hub end is securely affixed at one end of the file instrument and is adapted for gripping by an operator or attachment to a mechanical device such as a dental drill.

It is often necessary to repeatedly insert and remove various file instruments into the root canal of a tooth during root canal therapy. Extreme care must be taken to prevent penetration of such file instruments beyond the root canal apex in order to avoid injury and possible infection of the adjacent periodontal tissue and bone structure. The file must be inserted no more than a specific maximum distance inside the root of the tooth. The occurrence of errors in depth penetration of the file into the root canal, either too deep or too shallow, are major causes of failure in endodontic procedures. Thus, it is important in the preparation of the root canal to control the working length of the file utilized. Since it is physically impossible for a practitioner to see inside the tooth to the root apex, a determination must be made as to how far the file can enter the root.

Before a file instrument is inserted to remove the pulp material, the length of the root canal is determined to identify a suitable working length for the file instrument. Generally, the working length is the distance from a fixed reference position on the crown of a tooth to or near the apical constriction opening of the root canal. Typically, a practitioner initially ascertains the depth through which the various sized root canal instruments should penetrate into the root canal by utilizing an x-ray of the tooth. A full scale x-ray of the tooth is taken and the insertion distance is measured on the developed x-ray photograph by measuring the length of the tooth involved, as well as the length of the root canal therein.

A significant problem that can result from root canal cleaning is apical perforation from insertion of a file or shaft of a file instrument to the apex of the root canal. Perforating the apex can result from an error in estimating or measuring the length of a root canal. Similarly, the apex can be perforated by extrusion of infected pulp material through the apex due to the force exerted by the file on the pulp material as the file is pushed downward to reach the apex. In addition to exposing the tissue surrounding the tooth to the infected pulp material, apical perforations also substantially complicate subsequent filling of the root canal with a filling or obturating material.

Various techniques and devices have been developed for limiting the depth of penetration of dental instruments to the root canal tip. For example, once the length of the root canal has been determined, it is possible to use a dental instrument having a file extending beyond the handle by the predetermined maximum allowable length.

More commonly, an adjustable stopper has been typically placed over each dental instrument along the shaft or file so that the distance between the tip of the instrument and the stopper equals the distance between the top or the occlusal surface of the tooth and the apex of the root canal. Thus, the stopper sets the root canal instrument to the proper length or penetration depth for the root canal. The stopper located at the proper point along each root canal instrument intended to be used ensures that the instrument is inserted the proper depth into the root canal.

Examples of instruments utilizing stoppers are shown in FIG. 1 and FIG. 2 respectively at 10 and 20. Instrument 10 has a peanut-shaped handle 12 which is particularly adapted to be gripped by a practitioner during a root canal procedure. Handle 12 is accordingly typically used for manual filing. Instrument 20 has a latch handle 22 for attachment to an endodontic handpiece for rapid rotation as shown in FIG. 3 at 60. Another example of an endodontic instrument with a latch attachment end is shown in British Patent No. 2,059, 778. A stopper 40 is shown positioned on file 14 of instrument 10 and on file 24 of instrument 20. Such stoppers are typically formed of a simple block of rubber or plastic material, or constructed of a housing and a compression spring. In addition to a single stopper as shown in FIG. 1 and FIG. 2, several movable stoppers may be utilized and positioned on the shaft such that one stopper abuts the handle. An additional example of an endodontic device utilizing stoppers is disclosed in U.S. Pat. No. 5,154,611 to Chen.

The position of the stopper on the file determines the working length of the instrument, which is the length of the file to be inserted into the tooth during treatment. As shown in FIG. 4, stopper 40 prevents further penetration of file 24 into the root canal of the tooth when the bottom surface of stopper 40 abuts the occlusal surface of the tooth 90 being treated, such as the incisal edge or cusp tip. In this manner, when the dental instrument enters the root canal, the dentist can limit insertion by observing the contact of the stopper at the edge of the tooth.

Since a variety of file instruments are used throughout the root canal procedure, conventional practice has been to individually measure and position the stoppers on the various implements used. It is frequently necessary for the dentist to fit a stopper on the dental instrument while the patient's mouth is held open. Thus, it is desirable that the operation be carried out as fast as possible. At the same time it is essential that stoppers be placed with perfect accuracy, as otherwise the possibility of poking the instrument beyond the tooth is presented.

The problems with the conventional stopper procedure are numerous. The individual measurement and placement of the stoppers on the dental instruments is very time-consuming and at times somewhat inaccurate. Each individual instrument and its stopper must be separately gauged against a separate scale or ruler and then individually set to the length indicated in an x-ray photograph. This procedure can involve inherent inaccuracies and a great deal of time and inconvenience to the dentist. In addition, there is also the potential for introduction of contaminants on the instrument during placement of a stopper thereon.

Further, the stoppers can be easily displaced or can slip from their intended position on the file instrument during use within the limited area of a patient's mouth and considering the relatively small size of the instruments involved. This can result in perforation of the apex of a tooth from failure of a stopper to remain at a predetermined position. It can also be difficult for the endodontist to precisely judge when the stopper has reached the surface of the tooth. Additionally, rubber stoppers may also be both flexible and movable and can therefore allow the file to proceed deeper into the root canal than may be desired.

Other devices have also been developed to limit the penetration of dental instruments into a root canal. For example, screw threads have been placed on the shaft of a file, with a nut threaded onto the file to act as a stopper. The manipulation of the file within a patient's mouth, however, can easily result in the nut being moved on the shaft.

In U.S. Pat. No. 4,028,810 to Vice, a root canal file is disclosed that includes a handle portion adjustably mounted in telescoping relation to the shaft of an elongated tool, with cooperating grooves in the shaft and handle preventing relative movement therebetween during use. The grooves around the shaft cooperate with mating ridges or grooves within the jaws of a tightening chuck on the handle to firmly interlock the handle and the shaft in any desired adjustment position.

Another endodontic instrument, disclosed in U.S. Pat. No. 4,165,562 to Sarfatti, includes a threaded base with a locking structure thereon and an elongated file projecting outwardly from the base. A threaded sleeve which acts as a stopper receives the base to facilitate longitudinal adjustment of the file relative to the sleeve. A plastic cap fits over the combination of the file and the sleeve and is imprinted with a plurality of graduations thereon to indicate the distance that the bottom of the file extends from the bottom of the sleeve.

While the above devices can limit the penetration of dental instruments into a root canal they are not adequately simple to use and manufacture. More importantly, however, conventional dental instruments do not provide a secure stopping capability while simultaneously enabling an instrument to be used with varying working lengths. Accordingly, there is a need for an improved endodontic device that overcomes or avoids the above problems.

SUMMARY AND OBJECTS OF THE INVENTION

The present invention has been developed in response to the present state of the art and, in particular, in response to problems and needs that have not been fully or completely solved by currently available endodontic instruments. It is an object of the present invention to provide dental instruments which may be positioned in an endodontic handpiece head such that the instruments have varying working lengths for use during an endodontic procedure such as root canal therapy. It is an additional object of the present invention that a secure stopping capability be provided by such dental instruments and/or the handpiece holding the instruments. It is a further object of the present invention that the length variations be identifiable by viewing the instrument in the chuck of an endodontic handpiece head. It is another object of the present invention that the working length of the instrument be variable in uniform increments. Finally, it is an object of the present invention that such instruments be simple to use and manufacture.

Features of the invention are briefly described hereinbelow. The dental instrument includes a file extending from a handle configured to enable the working length of the handle to be varied. The handle of the instrument is adapted to be received in and to be releasably held by a chuck or collet of an endodontic handpiece head. Both the handles and chucks are adapted to enable the handles to be appropriately positioned in the chuck of a dental handpiece at various positions to yield a desired working length and to then be secured.

The need for rubber stoppers is eliminated since the handle is securely held by the chuck such that the instrument has varying working lengths which remain securely fixed during an endodontic procedure. Accordingly, a practitioner can use the present invention without worrying that the working length will change during use due to slipping of a rubber stopper or movement of the handle relative to the chuck. Additionally, the rim around the chuck is preferably configured to act as a stop during use of the handpiece in an endodontic procedure.

In using the dental instruments, an instrument is selected which has an approximately appropriate file length. The working length of the instrument can then be varied by positioning the handle of the instrument into a chuck of a handpiece and then securing the handle in the chuck to provide a desired working length. More particularly, the instrument is adjusted to a desired position with respect to the chuck by pushing the handle of the instrument further into the chuck or by pulling the instrument out until the correct position is obtained. This eliminates the need for multiple instruments having many different working lengths.

The chuck has retention arms which are preferably rounded in order to be applied in a rated configuration with the flat cylindrical surfaces of the handle. The retention arms of the chuck are configured to press against the handle in order to hold the chuck.

The file and/or the handle may have incremental adjustment indicators such that the working length can be determined by viewing the incremental adjustment indicators. The indicators may be distinctive portions of the file or handle. The distinctive sections preferably have uniform lengths, such as 1 mm, to enable the user to move the handle in distinct uniform increments.

The incremental adjustment indicators may be markings that extend around the perimeter of the file and/or handle as bands or as lines around only a portion of the perimeter. The markings may all be the same color or each marking may have a different color. Such markings may be printed or may be formed by other suitable methods. For example, the handle may have markings formed by two color molding processes. Similarly, the handle may have distinct sections formed by two color molding processes. The handle may also have distinct sections that are identified by different handle diameters or configurations. For example, the bottom of the handle may have a section, referred to herein as a gripping section, which is configured for engagement with the retention arms of the chuck and which is sandwiched between two distinct sections. More particularly, the gripping section may be sandwiched between a bevelled section which tapers toward the file and a section which is slightly recessed compared with the gripping section.

Alternatively, the handle and retention arms may also be configured such that it is possible to move the handle only in discrete uniform increments. It is also possible use a handle with no incremental adjustment indicators and to then use a gauge or similar device to measure the working length of the instrument.

The file of the instruments may have any suitable configuration. However, the files are preferably configured for use in cleaning the operative middle portion of the root canal which is the portion of the anatomical root canal above the apical portion. Other instruments can then be used to clean the apical portion. The methodology described herein for cleaning the operative middle portion involves using the contours of the operative middle portion as a guide for movement of the file. The file is accordingly moved around the perimeter of the root canal or moved from side to side while the instrument is flexed against the root canal surfaces. This movement is rather aggressive so the methodology is particularly benefited by the secure stopping action provided by the rim of the endodontic handpiece head.

The present invention is advantageous in that the length of the dental instrument can be quickly adjusted in a simple manner and such instruments are simple to manufacture. This ability is further enhanced by the ability to identify the length variations by merely viewing the instrument in the chuck of an endodontic handpiece head when the file and/or the handle has incremental adjustment indicators, particularly uniform incremental adjustment indicators. Another advantage is the elimination of the need for rubber stoppers through the use of the rim of the endodontic handpiece head. Additionally, it decreases the number of instruments needed for completing conventional root canal therapy procedures as some practitioners prefer to have as many instruments having fixed lengths as are necessary to work within typical root canals without rubber stoppers.

These and other objects, features and advantages of the present invention will become more fully apparent from the following description and appended claims, or may be learned by the practice of the invention as set forth hereinafter.

BRIEF DESCRIPTION OF THE DRAWINGS

In order to understand the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE INVENTION

The present invention is directed to an endodontic instrument configured to have a working length that can be varied. More particularly, the working length is varied by securing the handle of an endodontic instrument in a chuck or collet of a dental handpiece at various positions. Both the handles and chucks are adapted to enable the handles to be appropriately positioned to yield a desired working length and to then be secured. Additionally, the rim around the chuck is preferably configured to act as a stop during use of the handpiece in an endodontic procedure.

Root canal therapy typically involves cleaning and enlargement of the root canal prior to applying an inert sealant. In many endodontic operations, it is necessary to successively insert an elongated instrument into, and then pull the same from, the root canal of a tooth in order to thoroughly remove any inflamed or necrotic tissue therein and properly enlarge the root canal. The length of the instrument is important as the endodontist must be careful not to extend the instrument beyond the apex of the root canal in a tooth to avoid exposing the tissue surrounding the tooth to infected material or pushing infected matter into the surrounding tissue. An appropriate length is determined by taking an x-ray or a sonic reading of the tooth to be treated.

FIGS. 5A–8 depict examples of instruments suitably adapted for use with an endodontic handpiece to provide varying working lengths. Each instrument has two primary components including a handle and an elongated working member or file configured to extend from the handle. The file can have any suitable configuration for use in root canal therapy or other endodontic procedures. Each instrument is discussed in detail hereinbelow.

In using the dental instrument of the invention, the length of the root canal is first determined and then an appropriate instrument is selected. More particularly, an instrument is selected based on the length of its file. The file length needs to approximately correspond with the length determined as necessary for working in the root canal. The working length of the instrument can then be increased or decreased by varying the position of the handle of the instrument in a chuck of a handpiece and then securing the handle in the chuck. The position of the handle with respect to the chuck is varied by pushing the handle of the instrument further into the chuck or by pulling the instrument out until the correct position is obtained. The instrument can then be effectively used during an endodontic procedure. Use of the instruments with handpieces is discussed hereinbelow in relation to FIGS. 11–14.

Figure 5A:
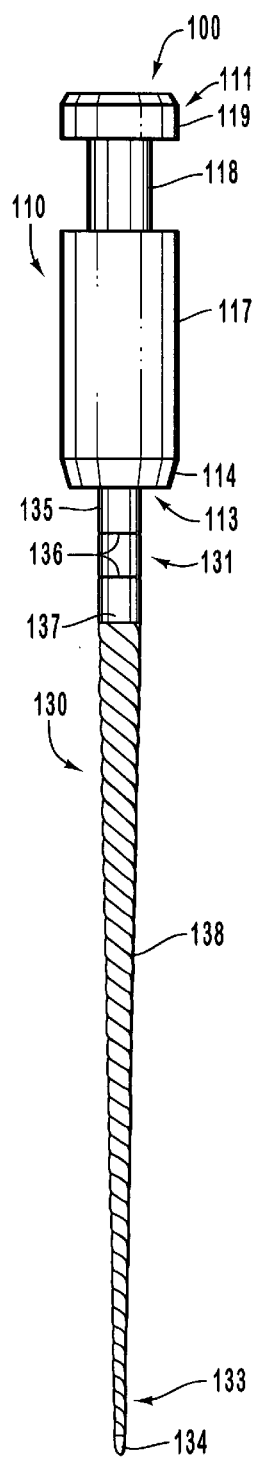
FIG. 5A is a perspective view of an instrument 100 having a handle according to the present invention.
Figure 5B:
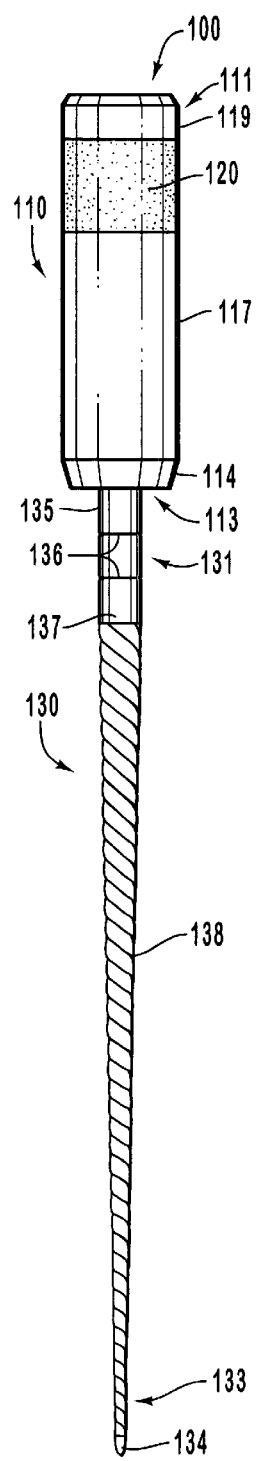
FIG. 5B is a perspective view of the instrument 100 shown in FIG. 5A having an identification band.

FIGS. 5A–5B depict an endodontic dental instrument 100 according to one embodiment of the invention. The dental instrument 100 includes a handle 110 and a file 130 which extends from handle 110.

Handle 110 has a top end 111 and a bottom end 113. Beginning at bottom end 113, there is a bevelled section 114 followed by a gripping section 117. FIG. 5A shows a band groove 118 interposed between gripping section 117 and top gripping section 119 of handle 110. Handle 110 is one example of a handle means for operatively moving a file to facilitate an endodontic procedure. The other handles disclosed herein are also examples of such handle means.

Instrument 100 as shown in FIG. 5B differs from that shown in FIG. 5A by the identification band 120 positioned within band groove 118. Instruments such as instrument 100 are typically sold in sets wherein the files of the instruments have different lengths. To identify the length of file 110, identification band 120 is provided which preferably has a particular color associated with the length of the file. Accordingly, a set of instruments may be provided which have files of varying lengths and differently colored identification bands to indicate the length of the files in the set. Identification band 120 is an example of a means for visually identifying the length of the file.

The handle may have any appropriate length which enables it do be moved within the chuck and then to be securely held. Handle 110 is preferably about 8.5 mm so that it can move up to 3 mm within the chuck of an endodontic handpiece that is 11.5 mm deep and still be flush with the rim of the handpiece as discussed below in reference to FIGS. 11A, 11E and 14A–14B. Alternatively, the handle may have a longer length such as handle 210 shown in FIG. 6 which is about 12 mm long. The width of the handle is preferably minimized to enable the endodontic handpiece to also have as small of a head as possible for enhanced maneuverability within a patient's mouth. The handle 110 can be made from any suitable material such as various metals or plastics.

File 130, which extends from top end 111 of handle 110, is an example of an elongated working member adapted for use in an endodontic procedure. The elongated working member may have any cutting configuration known for use as a reamer, bit, broach, or as a similar instrument. File 130 has a proximal end 131 opposite a distal insertion end 133 which terminates at a narrow tip 134. File 130 has a shank portion 135 which transitions to an abrading portion 138. The visible portion of file 130, which is the portion extending from handle 110 is the working portion of file 24. The working length of the instrument, however, is determined by the manner in which the handle is positioned in a chuck of a handpiece.

The diameter of file 130 is small enough so that file 130 can be easily inserted into a root canal of a tooth during an endodontic procedure. Generally, file 130 has a diameter in a range from about 0.06 mm to about 2 mm. File 130 is preferably made from a high strength resilient metal, such as stainless steel, capable of sufficient flexing to follow the normal curvatures of a root canal in a tooth and has an abrasive surface. File 130 can, however, be made of any suitable material such as nickel/titanium File 130 is an example of a file means for removing and cleaning pulp material from a root canal during an endodontic procedure in an abrasive action. The other files disclosed herein are also examples of such file means.

Figure 5C:
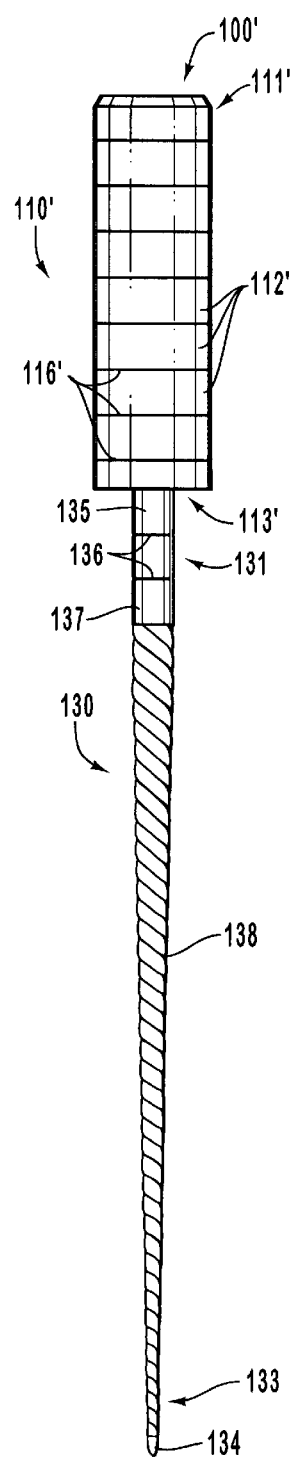
FIG. 5C is a perspective view of another embodiment of an instrument 100' having a handle and a file configured in accordance with the present invention with incremental adjustment indicators.

As indicated above, file 130 has a shank portion 135. Shank portion 135 has a series of gradient or hatch markings 136 formed thereon. Markings 136 may be spaced at any desired increment such as 1 mm increments as shown in FIGS. 5A–5C or in smaller increments such as 0.5 mm to divide shank portion 135 into incremental adjustment sections 137. The markings 136 are used to make incremental adjustments of handle 110 to a desired position with respect to a chuck of an endodontic handpiece when the dental positioned for use in an endodontic procedure.

Shank portion 135 has a length of 3 mm with three incremental adjustment sections 137 so that instrument 100 can be moved 1–3 mm within the chuck of an endodontic handpiece in 1 mm increments. When an instrument configured like instrument 100 is used, it is preferably to select an instrument with a length that is no greater than 3 mm than the determined length of the root canal. Selecting an instrument like instrument 100 with such length enables the bottom end 113 of handle 110 of instrument 100 to be either flush with the rim of the handpiece or to be pushed up in the chuck of the handpiece up to 3 mm so that the instrument is inserted into the root canal without perforating the root canal.

Markings 136 may all be the same color or each band may have a different color. Markings 136 may be printed or etched onto the shank portion 135 of file 130 by any suitable method. The markings may also be small recesses formed into the shank portion of the file without any coloring. While the markings are shown extending around the perimeter of the file, the markings may also be hatch markings which appear on only a portion of the perimeter such that the markings are viewable from only a side of the handle. The sections may also have submarkings to indicate subincremental lengths such as 0.5 mm lengths.

Markings 136 as shown in FIGS. 5A–5C are examples of incremental adjustment indicators. Such indicators are also examples of incremental adjustment indicator means for indicating the working length of an instrument once the handle is held within a chuck of an endodontic handpiece head. When such indicators are uniformly spaced as shown then the indicators are also examples of uniform incremental adjustment indicators and uniform incremental adjustment indicator means for indicating the working length of an instrument once the handle is held within a chuck of an endodontic handpiece head. Note, however, that the markings can also be formed on the file in nonuniform increments such as 1 mm, 1 mm, 1 mm and then 2 mm While such a combination as a whole is not uniform it does include some uniformly spaced gradient markings. Such a combination is accordingly an example of nonuniform incremental adjustment indicators as well as incremental adjustment indicators which include uniform incremental adjustment indicators.

Figure 11A:
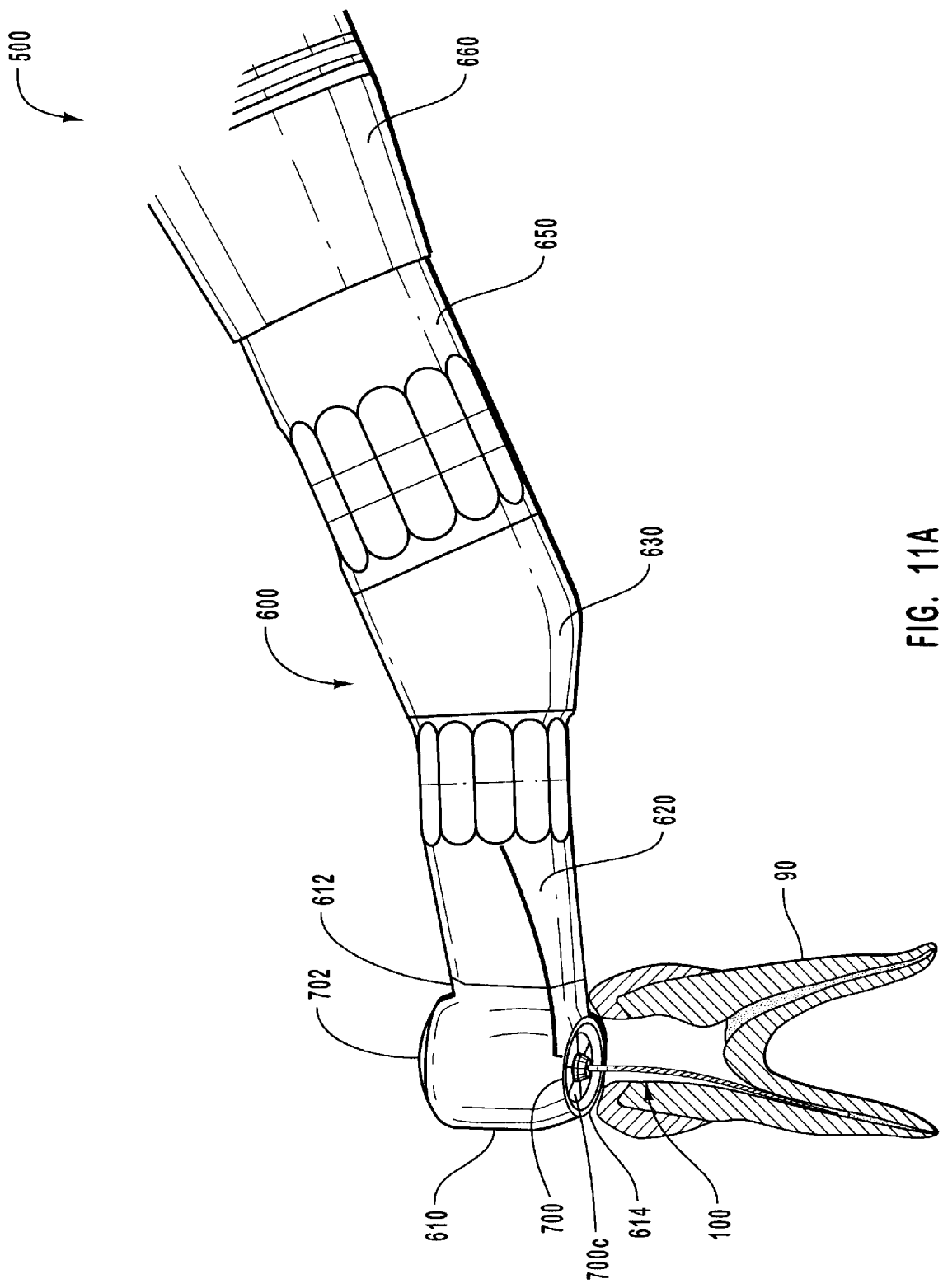
FIG. 11A is perspective view of a handpiece having a chuck which holds an instrument 100 as the instrument 100 is moved within a tooth, which is shown in a cross-sectional view.
Figure 11B:
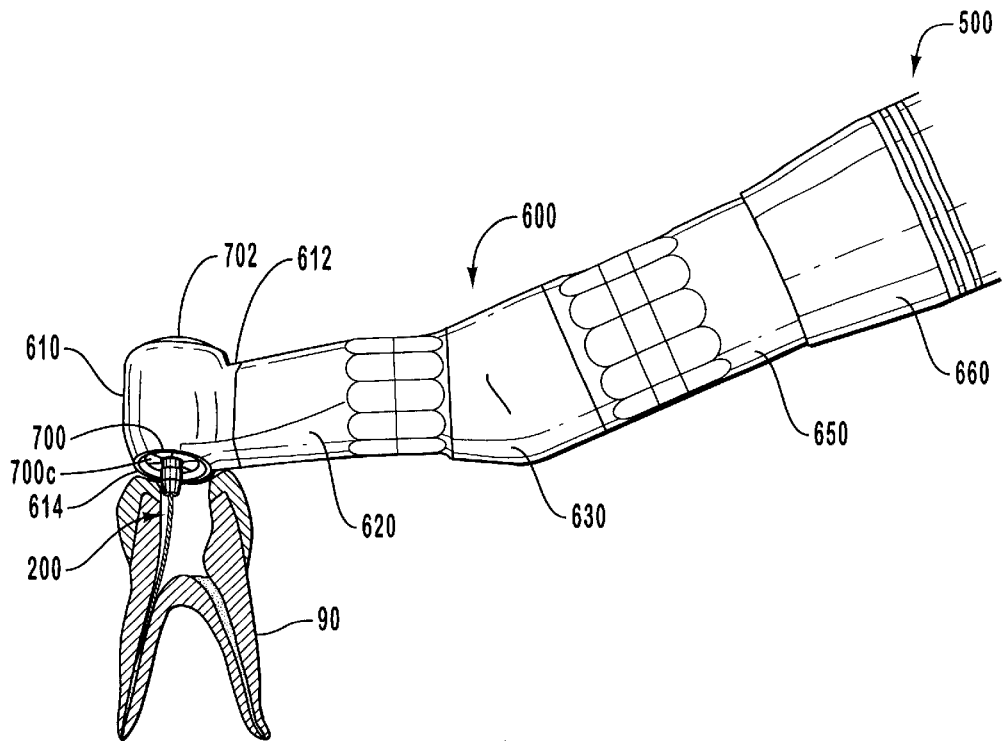
FIG. 11B is perspective view of a handpiece as shown in FIG. 11A with an instrument 200 held in its chuck as the instrument 200 is moved within a tooth, which is shown in a cross-sectional view like FIG. 11A.
Figure 11C:
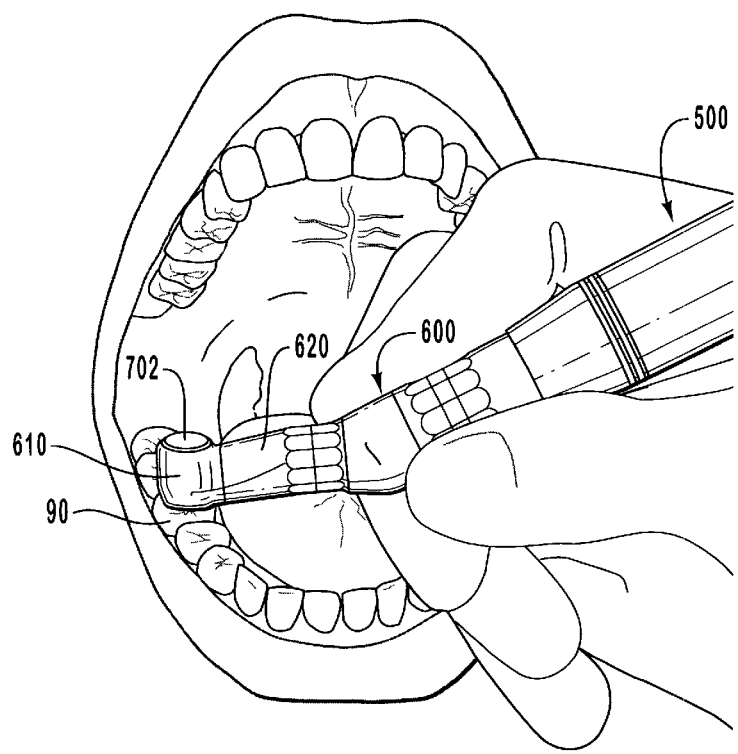
FIG. 11C is a perspective view of the endodontic handpiece shown in FIG. 11A being used in an endodontic procedure.
Figure 11D:
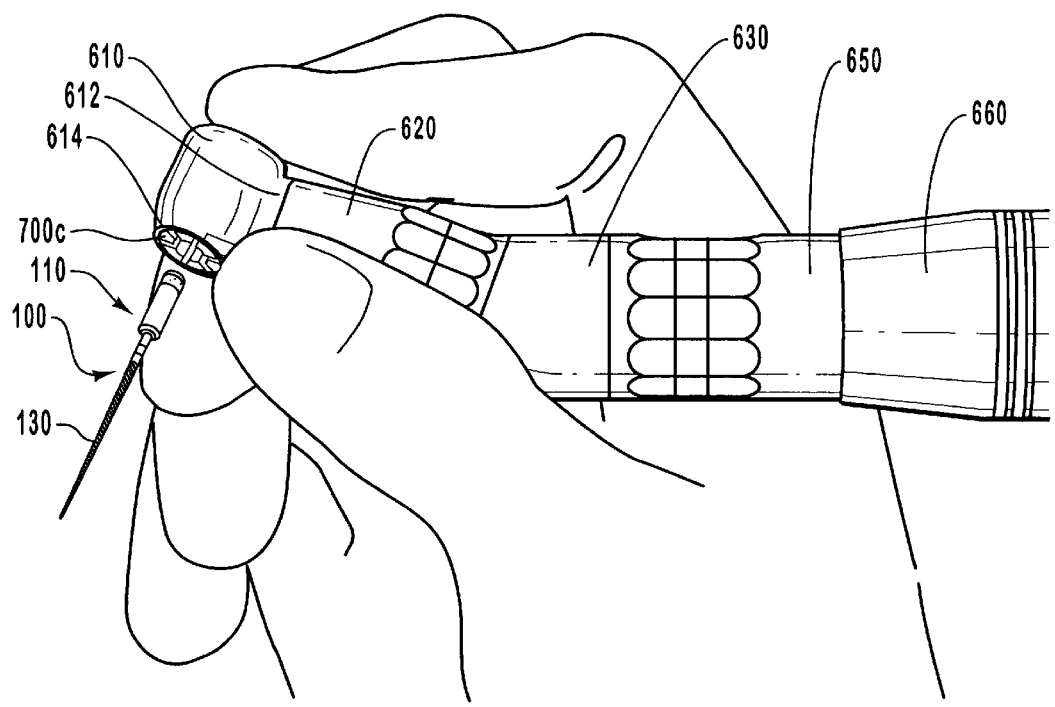
FIG. 11D is a perspective view of a users hand depressing a cap to lower the chuck into an open position to receive the handle of the instrument 100.
Figure 11E:
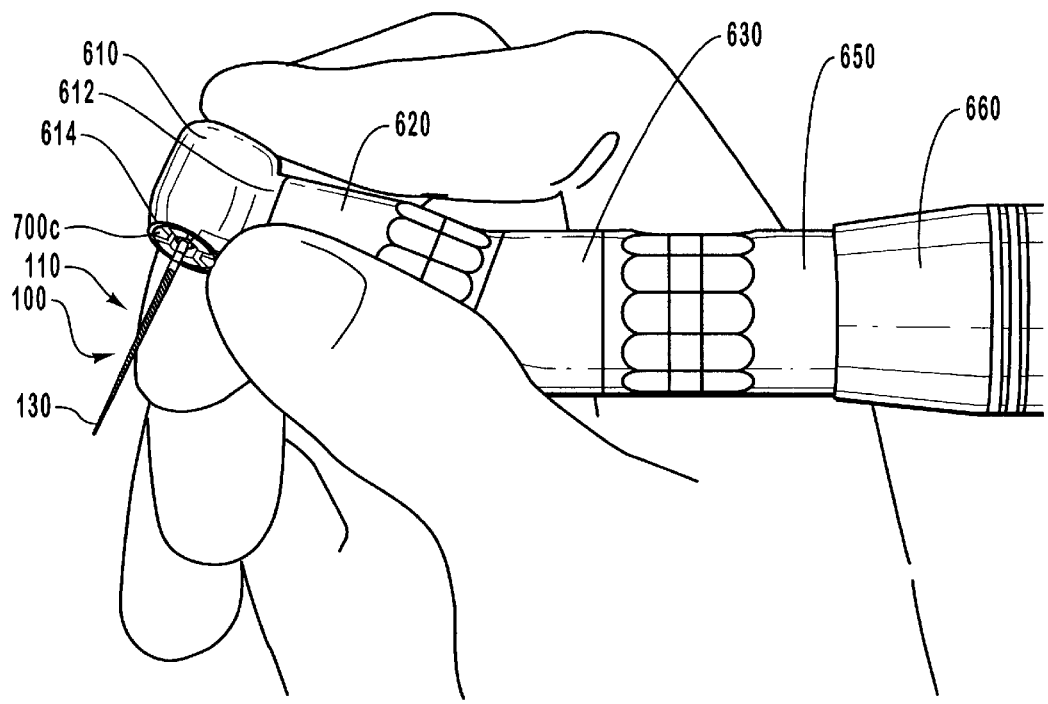
FIG. 11E is a perspective view of a chuck in a closed or engaged position securely holding the handle of the instrument 100 after a cap has been released.

Instrument 100 depicted in FIGS. 5A–5B is designed so that the bottom end 113 of handle 110 is preferably either flush with the rim of a handpiece head positioned around the chuck as shown in FIG. 11A or is positioned in the chuck as shown in FIG. 11E. When the handle is held in the chuck such that part of the file extends into the chuck, the handle is preferably positioned such that one of the markings 136 is flush with the rim. If one of the markings is not flush with the rim then it is necessary to measure the working length of the file which is the portion of the file extending beyond the rim. Similarly, if the instrument is positioned such that its handle extend beyond the rim of the handpiece head then it is necessary to measure the working length of its file.

Figure 9:
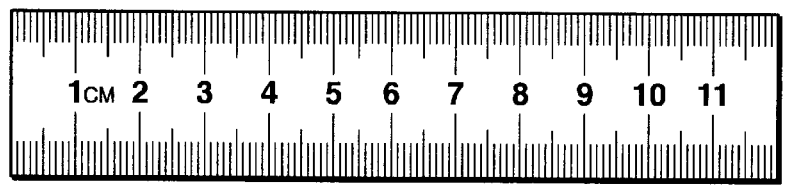
FIG. 9 is a perspective view of a ruler which can be used to measure the working length of an endodontic instrument.

There are several devices and methods which are useful for measuring the working length of a file of an endodontic instruments. For example, a ruler having a millimeter scale offers a simple mechanism to quickly measure the working length as shown in FIG. 9 and as disclosed in U.S. Pat. No. 3,772,791 issued to Malmin. The ruler may, for example, be transparent or be stainless steel. The ruler may also be configured to be worn as a ring on a thumb or finger. An example of such a finger worn ruler is disclosed in U.S. Pat. No. 4,976,615 issued to Kravitz and in U.S. Pat. No. 4,280,808 issued to Johnsen et al. The above patents are all incorporated by reference.

Figure 10:
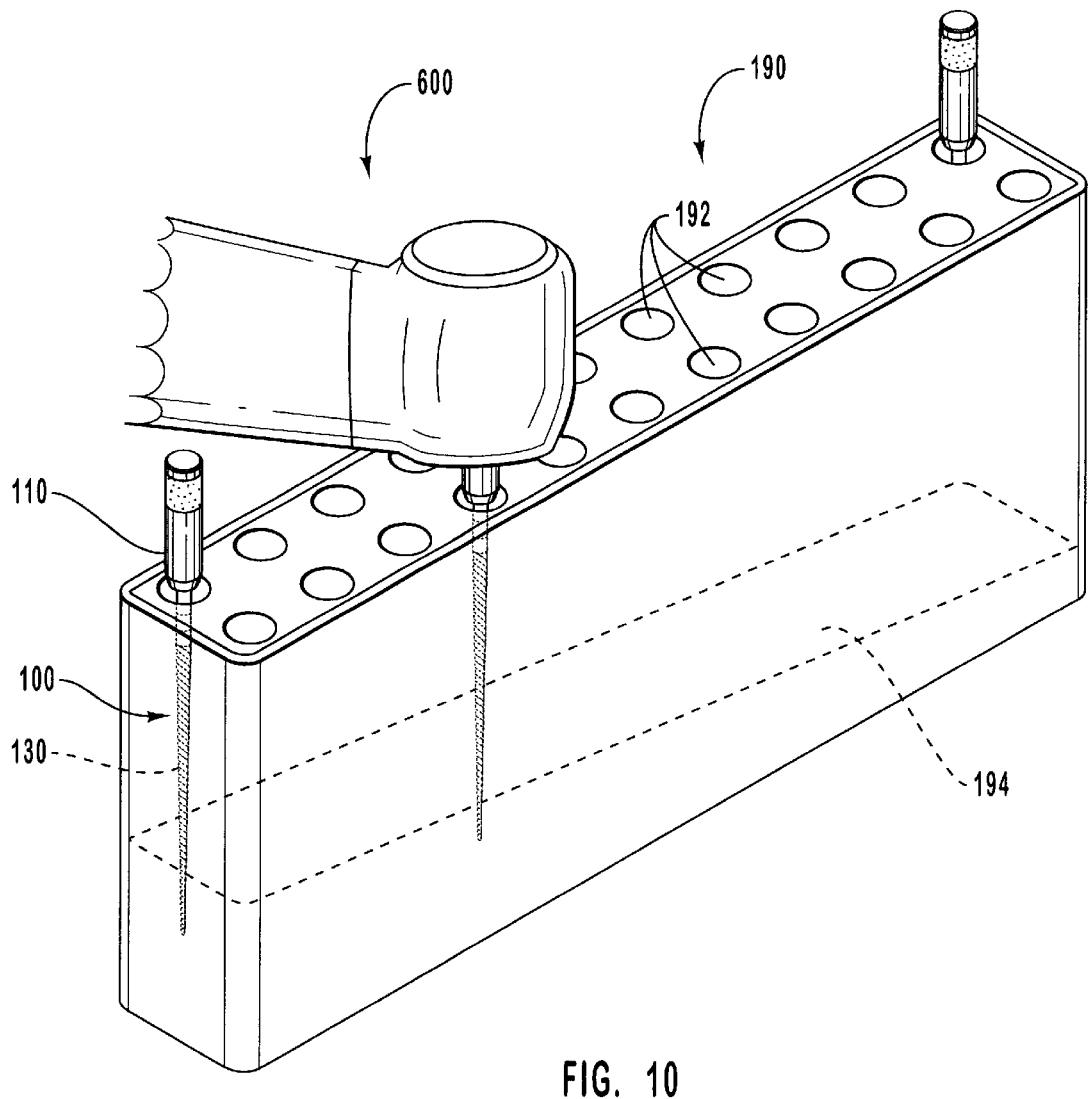
FIG. 10 is a perspective view of a gauge which can be used to measure the working length of an endodontic instrument.

There are also many gauges presently sold which enable a practitioner to insert an instrument and obtain a measurement of the working length. One example of such a gauge is a measuring block as shown in FIG. 10 at 190 having a plurality of holes 192 in the top of the block which extend into a chamber defined by a wedge 194. Once an instrument is inserted into a hole such that the tip encounters the tapered chamber, the length is identifiable by the position of the hole relative to the other holes. Similarly, U.S. Pat. No. 3,938,253 issued to Barnard et al. discloses the use of two circular plates arranged in coaxial spaced apart disposition with one plate having a series of through holes therein to each receive a respective instrument with the tip thereof resting on the other plate. Additional examples of appropriate gauges are disclosed in U.S. Pat. No. 4,182,040 issued to Bechtold and in U.S. Pat. No. Des. 292,021 issued to Stoll. The above patents are all incorporated by reference. Such rulers and gauges are examples of means for measuring the working length of an endodontic instrument.

Handle 110 does not have gradient markings like markings 136 so it is not possible to move the handle such that the bottom end 113 of handle 110 extends beyond the rim of an endodontic handpiece head with a particular incremental length other than the length of bevelled section 114 which is 0.5 mm. However, handle 110' of instrument 100' in FIG. 5C depicts an example of a handle having gradient or hatch markings 116' that enable the handle to extend beyond the rim of an endodontic handpiece head in distinct increments. Note that handle 110 can of course also be configured with markings like markings 116' on gripping section 117.

The markings 116' of handle 110' divide handle 110 into incremental adjustment sections 112'. Since instrument 100' has markings on both its handle 110' and on the shank portion 135 of its file 130, it has more incremental positions. More particularly, the handle can be pushed up into the chuck, extend from the chuck or be positioned such that its bottom end 113' is flush with the rim of an endodontic handpiece head. However, as explained below, it is preferably to use only the markings on the file such that the handle does not extend from the chuck to enable the rim of the endodontic handpiece head to act as a stop.

Both handle 100 and handle 100' are within the scope of the present invention as both handles are able to move within a chuck to adjust the working length of the instrument. It is also possible to utilize an instrument that has a handle adapted for movement within a chuck and that has no markings on either its handle or its file for incremental adjustments. However, it would be necessary to measure the working length of such an instrument since it would not be possible to merely view the instrument and determine the working length as in other embodiments.

As indicated above, gradient markings 116' are used to make incremental adjustments of handle 110' to a desired position with respect to a chuck of an endodontic handpiece when the instrument is positioned for use in an endodontic procedure. Like markings 136, markings 116' may all be the same color or each band may have a different color. The markings may be formed on handle 110' by any suitable method such as printing. Additionally, when handle 110' is formed from plastic, two color molding processes may be used such that the markings 116' are formed as bands with one or more different colors than the remainder of handle 110'. Note that while the markings are shown extending around the perimeter of the handle, the markings may also be hatch marking which appear on only a portion of the perimeter such that the markings are viewable from a side of the handle.

Gradient markings 116' spaced uniformly as shown in FIG. 5C are additional examples of uniform incremental adjustment indicators and uniform incremental adjustment indicator means. Note that the incremental adjustment sections 112' are shown having uniform increments of 1 mm except for the adjustment section at top end 111' of handle 110 so that the length of the handle is 8.5 mm However, all of the incremental adjustment sections can also all be uniform The instruments shown in FIGS. 6–8 respectively at 200, 300 and 400 provides additional examples of an instrument with a handle configured for movement within the chuck of an endodontic handpiece. The instruments depicted in FIGS. 6–8 may be positioned in a chuck such that the bottom ends of their respective handles extend out of the chuck as shown in FIG. 11B. Of course, the instruments depicted in FIGS. 6–8 may also have their respective handle bottom ends held in the chuck flush with the rim of the handpiece head.

Figure 6:
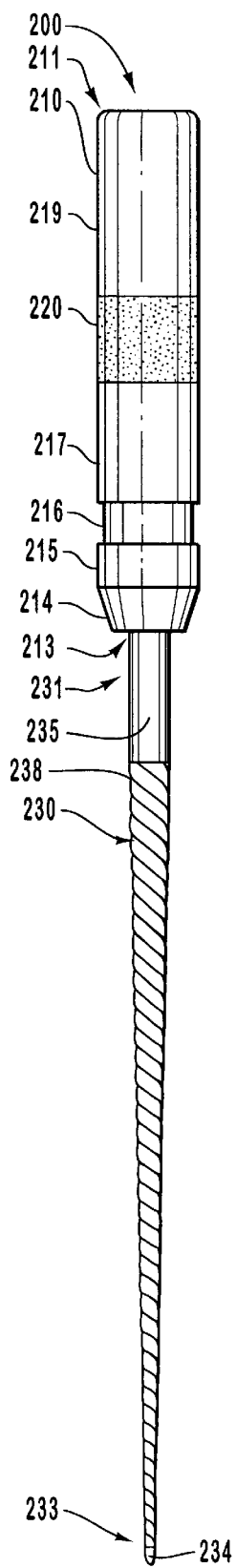
FIG. 6 is a perspective view of another embodiment of an instrument 200 having a handle configured in accordance with the present invention with incremental adjustment indicators.

Instrument 200 is shown in FIG. 6 having a file 230 extending from a handle 210. Handle 210 has several distinct sections which each have an incremental length and act as incremental adjustment indicators. Beginning at bottom end 213, there is a bevelled section 214 followed by a bottom gripping section 215. A shallow recess 216 is located between bottom gripping section 215 and a middle gripping section 217. A band groove 218 is interposed between middle gripping section 215 and top gripping section 219 of handle 210, however, band groove 218 is not shown in FIG. 6 as an identification band 220 is positioned within band groove 218.

When an instruments configured such as instrument 200 is used, the user selects an appropriate instrument by determining which identification band identifies an instrument that has a file length within several millimeters of the determined length of the root canal or the length determined as being necessary. The demarcations on the handle, which are sections having incremental lengths, can then be used to fine tune the working length of the instrument. For example, bevelled section 214, bottom gripping section 215 and shallow recess 216 are each 1 mm long, thereby enabling a user to adjust the working length in 1 mm increments. If an adjustment is needed which is greater than 3 mm, it is preferable to use a different instrument having a file with a greater length. However, middle gripping section 217 has a length of 3 mm so handle 210 can be extended even farther out of a chuck. It is even possible to extend handle 210 out of a chuck such that the chuck holds only top gripping section 219 or top gripping section 219 and identification band 220. Identification band 220 and top gripping section 219 have lengths which are respectively 2 mm and 4 mm. Identification band 220 is sufficiently thick that its surface is essentially level with that of middle gripping section 217 such that when it is gripped within a chuck, pressure can be applied to the band groove 218 via identification band 220 as well as to top gripping section 219 and any sections below which are level therewith and within the chuck.

Two or more sections such as bevelled section 214, bottom gripping section 215, shallow recess 216, middle gripping section 217, band groove 218 and top gripping section 219 are additional examples of incremental adjustment indicators. Such indicators are also additional examples of incremental adjustment indicator means for indicating the working length of an instrument once the handle is held within a chuck of an endodontic handpiece head. Sections which all have the same incremental length such as bevelled section 214, bottom gripping section 215, shallow recess 216 which all have a length of 1 mm are additional examples of uniform incremental adjustment indicators. Such uniform incremental adjustment indicators are also examples of uniform incremental adjustment indicator means for uniformly indicating the working length of an instrument.

If handle 210 is held in a chuck such that part of middle gripping section 217 is extending out from a chuck and the remainder is held within the chuck, then it may be necessary to measure the working length of instrument 100 in order to exactly identify the working length. Similarly, if the handle is completely uniform in cross-sectional shape and has no demarcations to indicate incremental variations in length it is not possible to accurately determine the length by viewing it. Accordingly, to identify the working length of an instrument with such a handle, it is necessary to measure the working length of the instrument as it for instrument 100 if its handle 110 extends more than 0.5 mm beyond the rim of the endodontic handpiece head. Accordingly, an instrument such as 100' that has a handle 110' with a markings 116' and a file with markings 136 provides for relatively large variations in the working length of the instrument 100. It is necessary to measure the working length of an instrument such as instrument 100' only if handle 110' is positioned in the chuck of an endodontic handpiece such that one of its markings is not flush with the rim of the endodontic handpiece head.

While it is possible for instrument 200 to be positioned such that the bottom end 213 of its handle 210 is within the chuck of an endodontic handpiece, such a use of instrument 200 is not preferred due to the length of handle 210. Handle 210 is longer than handle 110 so in order for handle 210 to be pushed up into the chuck of an endodontic handpiece the chuck must be longer than the handle of the instrument. An increase in the length of the chuck results in a taller handpiece head and reduces the mobility of the handpiece head. Since file 230 is preferably not moved into the chuck, file 230 has a shank portion 235 with no markings. Note that like file 130, however, file 230 has a proximal end 231 opposite a distal insertion end 233 which terminates at a narrow tip 234.

Figure 7:
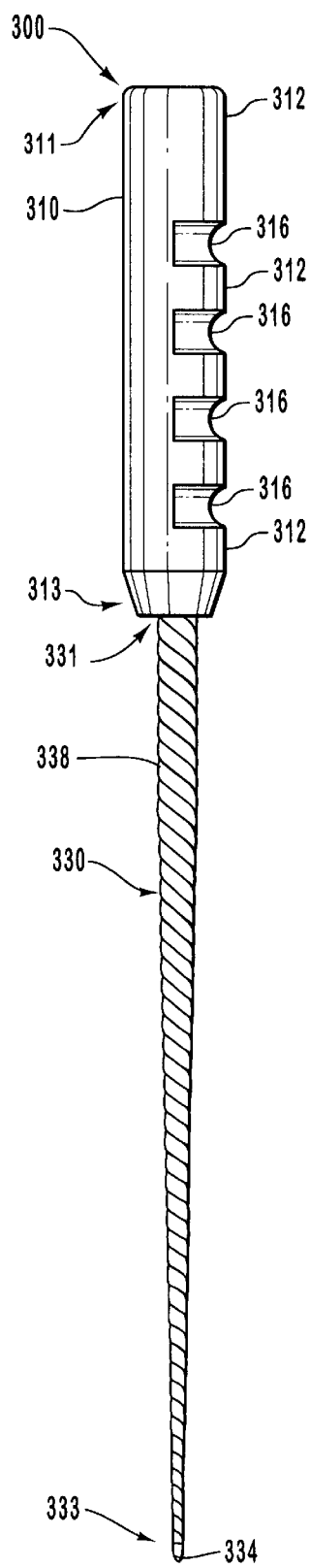
FIG. 7 is a perspective view of another embodiment of an instrument 300 having a handle configured in accordance with the present invention with incremental adjustment indicators that permit movement in only set increments.

Another embodiment of a suitable instrument is shown at 300 in FIG. 7. Like the other instruments, instrument 300 has a file 330 that extends from the top end 311 of its handle 310. However, unlike the files described above, file 330 does not have a shank portion. It is generally preferred to have a shank portion as it typically not necessary to abrade 1–3 millimeters of the uppermost portion of the root canal. Additionally, it is easier to include markings on the shank portion than it is on the abrading portion. However, file 330 is configured to abrade along its entire length as some methodologies utilize such a configuration to abrade a root canal with all of the surfaces of the file that extend from the handle.

Handle 310 has a series of grooves 316 located on one side of handle 310 which are in uniform increments. The remainder of handle 310 is a gripping section 312. Grooves 316 may be in any suitable increments such as in 1 mm increments. Grooves 316 may be formed by any suitable method. For example, handle 310 may be molded in a configuration such that it appears as shown. Additionally, grooves 316 may be formed by removing segments from a precursor to handle 310 by etching the surface or lathing a metal handle precursor. Similarly, a precursor handle can be rotated and brought into contact with a knife or suitable implement for removing segments thereof While grooves 316 are shown as only partially encircling the circumference of handle 310, it should be understood that grooves can be formed around the entire circumference of handle 310. Additionally, grooves 316 need not be curved as shown. The grooves may be replaced by recesses such as shallow recess 116 which have shallow walls which are perpendicular to the surfaces of the gripping sections. Grooves 316 and recesses as described above in relation to handle 310 are additional examples of uniform incremental adjustment indicators and uniform incremental adjustment indicator means.

Instrument 300 has a file 330 which extends from top end 311 of handle 310. File 330 has a proximal end 331 opposite a distal insertion end 333 which terminates at a narrow tip 334. The entire visible portion of file 330 is configured to abrade. The portion of file 330 located within handle 310, which is not shown, may be configured like a shank or be configured to optimally interlock or anchor file 330 in handle 310.

Figure 8:
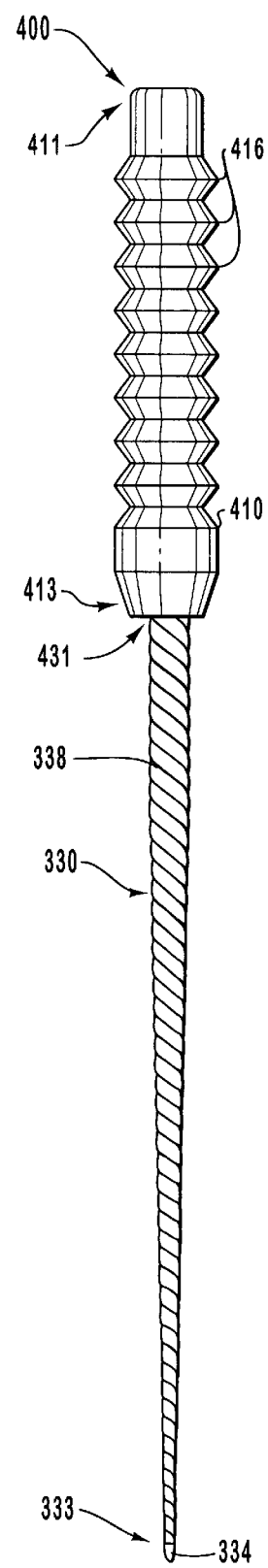
FIG. 8 is a perspective view of another embodiment of an instrument 400 having a handle configured in accordance with the present invention with incremental adjustment indicators that permit movement in only set increments.

FIG. 8 depicts another embodiment of an instrument at 400 having a handle 410 and a file 330 extending from a top end 411 of handle 410. Handle 410 has ridges 416 positioned at uniform increments along its length from top end 411 to bottom end 413 of handle 410. Handle 410 can be formed as shown by essentially the same methods used in the formation of handle 310. For example, handle 410 can be molded such that it has ridges 416 or the sections between ridges 416 can alternatively be removed by etching, cutting or lathing when handle 410 is formed from metal. While ridges 410 are shown having pointed tops or peaks, ridges 410 can also be formed to have rounded or sloped tops such that a chuck has a greater surface contact with the handle to hold the handle in position. It may, however, be more difficult to determine the working length of a handle having sloped ridges by merely viewing the instrument as the increments may not be as easily identified. Accordingly, an embodiment having sloped ridges may also have gradient markings to ensure that the length can be quickly determined. Ridges 416, as described above in relation to handle 410, are additional examples of uniform incremental adjustment indicators and uniform incremental adjustment indicator means.

Figure 11F:
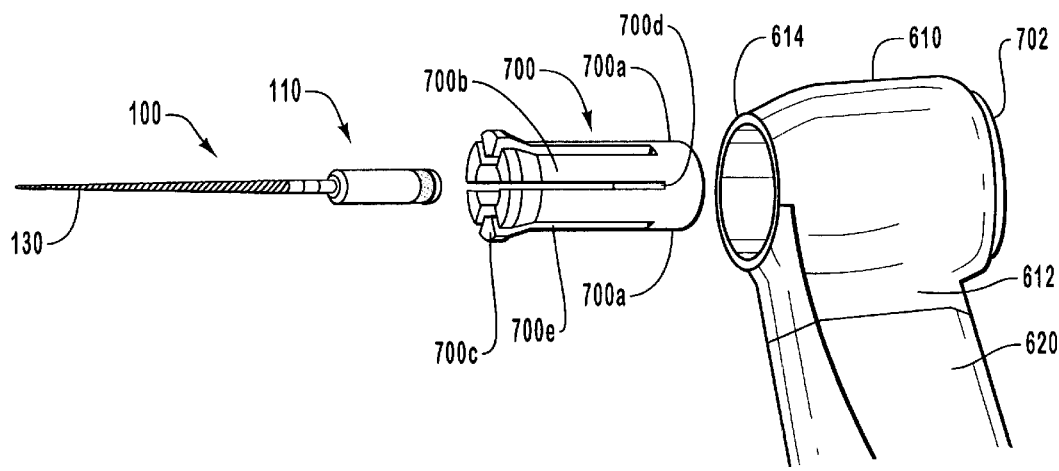
FIG. 11F is an exploded perspective view of a head element of an endodontic handpiece head, a chuck and the instrument 100.
Figure 12:
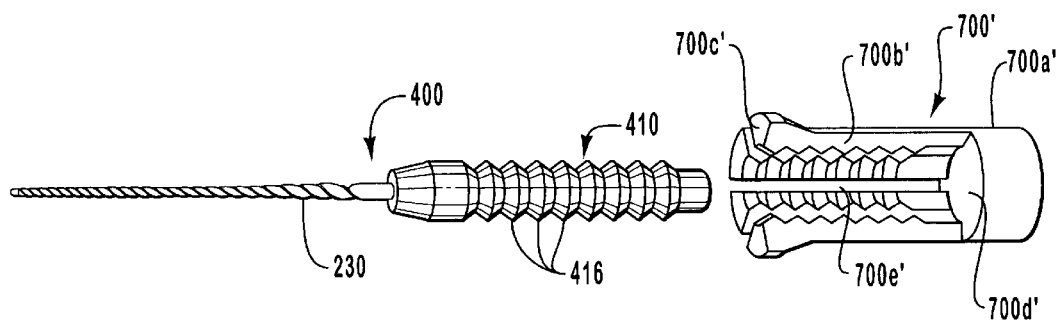
FIG. 12 is an exploded perspective view of the head element of an endodontic handpiece head as shown in FIG. 11E, another embodiment of a chuck and the instrument as shown in FIG. 8.

FIGS. 11A–14D depict a dental handpiece 500 used to couple with instruments such as those shown at 100, 200, 300 and 400. FIGS. 11A–11E depict the use of handpiece 500 and its primary features in relation to the use of endodontic instruments having handles configured to vary the working length of the instrument. FIG. 12 depicts an alternative embodiment. FIGS. 13A–13C depict in detail the elements of handpiece 500, particularly head 600 while the other component of handpiece 500, motor 800, is shown only in FIG. 13A as essentially any conventional motor may be coupled with head 600. FIGS. 14A–14B and FIGS. 14C–14D respectively show instruments 100 and 200 being used with handpiece 500 in tooth 940 in accordance with a particular methodology for cleaning root canals. Before describing the use of instrument 100 or instrument 200 in combination with handpiece 500 as shown in FIGS. 11A–11C, it is helpful to have an understanding of the primary components that enable the instruments to have varying working lengths by referencing FIGS. 11D–F.

FIG. 11F is an exploded perspective view of only a head element 610 of head 600, a chuck 700 held within head element 610, and instrument 100. The configuration of a chuck which receives and holds the handle of the instrument is most clearly viewed in FIG. 11F and the alternative embodiment shown in FIG. 12. Chuck 700 has various integral components or segments. Chuck 700 is shown having retention arms 700b which integrally extend from cylindrical portion 700a with spaces between each retention arm 700b. The flat terminal ends of the retention arms are referred to as flange portions 700c. Chuck 700 has a chuck base 700d at its terminal end opposite from the opening at the receiving end. Chuck 700 has a handle chamber 700e defined by retention arms 700b and chuck base 700d. FIG. 11F also most clearly shows the interface between retention arms 700b of chuck 700 and handle 110.

FIG. 11D and FIG. 11E show chuck 700 being utilized. FIG. 11D depicts a push button chuck mechanism being pushed such that chuck 700 is in an open position ready to receive handle 110 of instrument 100 at variable positions. Note that when cap 702 is pressed as shown in FIG. 11D, chuck 700 is depressed towards rim 614 and retention arms 700b of chuck 700 are expanded. FIG. 11E depicts chuck 700 in a closed or engaged position securely holding handle 110. After handle 110 is positioned within chuck 700 and cap 702 is released, retention arms 700b of chuck 700 clamp around handle 110 as shown in FIG. 11E.

FIGS. 11A and 11C depict instrument 100 being held by chuck 700 as handpiece 500 is used to clean the root canal of a tooth 90. Handle 110 is positioned within chuck 700 such that the bottom end 113 of handle 110 is flush with rim 614 and only bevelled section 114 extends beyond flange portions 700c of retention arms 700b. Accordingly, file 130 can be moved by handpiece 500 without concern for handle 110 as it is not possible for handle 110 to restrict or interfere with the movement of the file against the root canal surfaces of the tooth.

Most conventional instruments have handles with a length of about 12 mm. Since conventional instruments are held in only one position by the handpiece without referencing incremental indicators, conventional handpieces have handle chambers with depths that either correspond approximately with the conventional handle lengths or cause the handles to extend beyond their rims.

Chuck 700 is shown in FIG. 11F with a handle chamber 700e defined by retention arms 700b and chuck base 700d with a depth of about 11.5 mm. As indicated above, handle 110 is most preferably about 8.5 mm long so that it can be recessed up to 3 mm within handle chamber 700e. However, the length of the handle and the depth of the handle chamber may have a differential that is more or less than 3 mm.

While relatively short handles such as handle 110 are preferred since they can be recessed within a chuck such as chuck 700, handles may also be used which do extend out of the chuck beyond rim 614 as shown in FIG. 11B. FIG. 11B depicts chuck 700 holding handle 210 of instrument 200 in a configuration such that a portion of handle 210 extends below rim 614. Since handle 210 has a length of about 12 mm, it is prevented from being recessed within the chuck and always extends beyond rim 614. In FIG. 11B, bottom end 213 extends about 3 mm beyond flange portions 700c of retention arms 700b and is about 2.5 mm beyond rim 614.

Note that flange portions 700c do not extend to rim 614. More particularly, rim 614 extends about 0.5 mm further than flange portions 700c of chuck 700. However, the flange portions may be flush with the rim. The differential between the rim and the chuck may be slight as shown or the chuck may recessed such that the flange portions of the chuck are about 1 mm, 2 mm, etc. above rim 614.

Figure 14A:
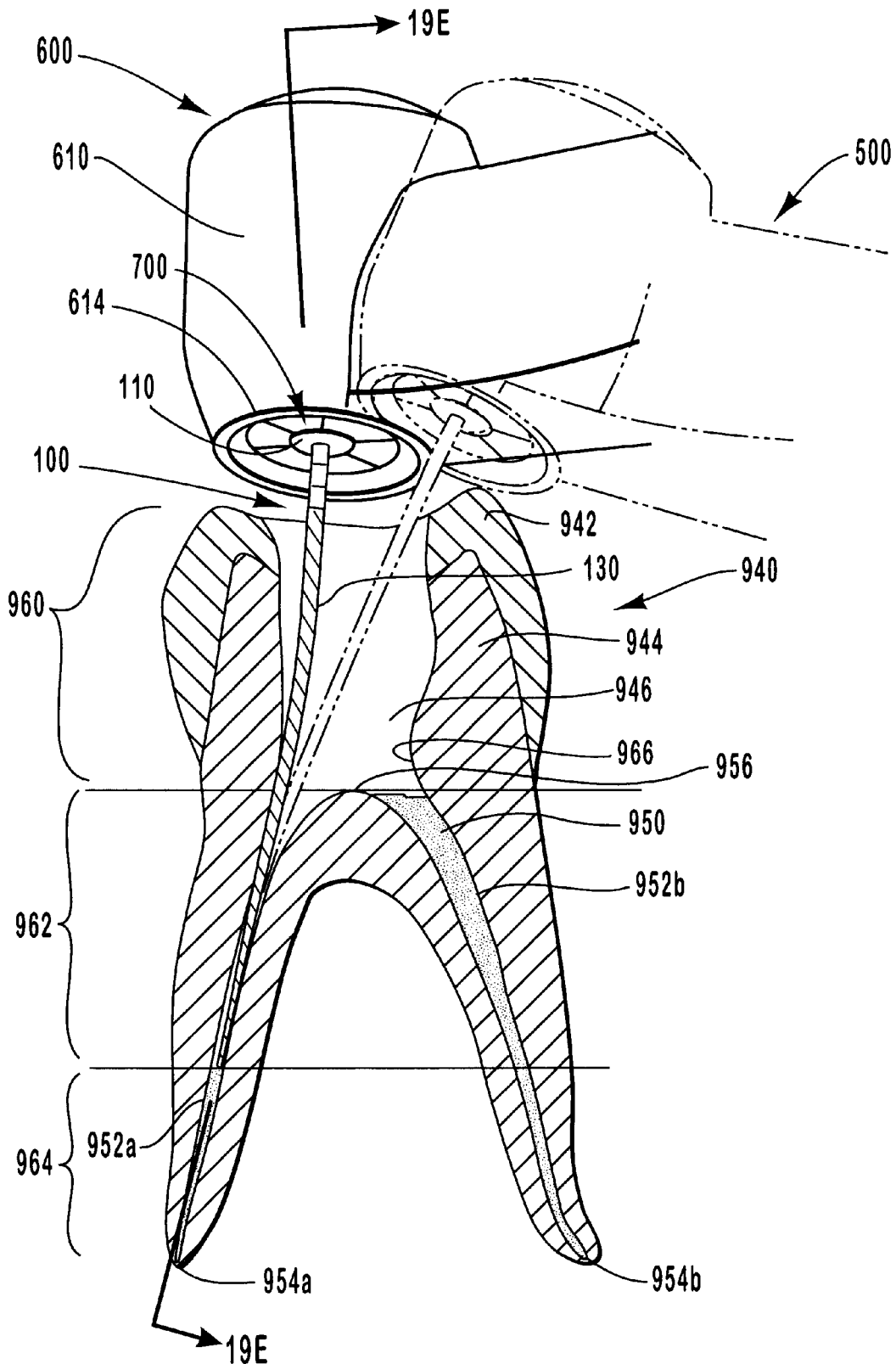
FIG. 14A is a longitudinal cross-sectional view of a tooth with a file portion of a file instrument 100 inserted into the root canal up to the apical portion.

As discussed below, the size of the head element is preferably minimized to increase the freedom of movement of the handpiece head. More particularly, it is helpful to minimize the overall height or vertical profile of the head element. As a result, the handle chamber preferably has a depth that is no greater than about 12 mm and that is preferably less than 12 mm. Since the instruments are preferably recessable within the chuck, the handle length is preferably less than 12 mm, more preferably less than about 10 mm, and most preferably no greater than about than about 9 mm The latchless configuration of the handles disclosed herein is in contrast to prior art handles such as handle 22 which require the use of a latch in the chuck to hold and rotate the handle. Since the handles are latchless, the handle can be engaged at various positions in the chuck. As discussed above, FIG. 11A shows handle 110 positioned such that its bottom end 113 is flush with rim 614 while FIG. 11E shows handle 110 further recessed such that its bottom end 113 is 1 mm above the retention flanges 700c. Similarly, FIG. 14A depicts bottom end 113 of handle 110 flush with retention flanges 700c. Any variation is permitted that is within the differential between the length of the handle and the depth of the handle chamber of the chuck.

FIG. 11F shows that once retention arms 700b of chuck 700 clamp onto handle 10, arms 700b are in an essentially parallel configuration with handle 110. The primarily uniform shape of handle 110 in combination with the parallel configuration of arms 700b when in the engaged position enables handle 110 to be firmly in chuck 700 at variable positions. More particularly, handle 110 is held by pressure exerted by retention arms 700b as the flat sidewall surfaces of handle 110 are contacted by or mated with the correspondingly flat retention arms 700b.

As shown in FIG. 11F, the diameter and the cross-sectional shape of the gripping sections of handle 110 are the same. Since identification band 120 is sufficiently thick to fill band groove 118 such that the surface of identification band 120 is level with the gripping sections 117 and 119, the only section of handle 110 which is not essentially the same between top end 111 and a bottom end 113 is bevelled section 114. Since handle 110 has a diameter and cross-sectional shape that are primarily uniform along its length, it can be easily held in a latchless configuration through pressure exerted by the endodontic handpiece head against the head. The term "latchless configuration" means that the top end of the handle is cylindrically shaped and that there are no features on the handle designed to lock the handle into only one position with respect to the chuck of the endodontic handpiece head.

Handle 210 also has a bevelled section 214 as well as a shallow recess 216 that do not have the same diameter as the main portions of the handle. Note however, that as shown in FIG. 11B, handle 210 can still be held firmly within chuck 700. Such a handle can also be easily held in a latchless configuration through pressure exerted by the endodontic handpiece head against the head since it has a diameter and cross-sectional shape that are substantially uniform along its length. More particularly, when shallow recess 216 extends out of chuck 700, handle 210 can still be held firmly within chuck 700 due to the length of the remainder of handle 210 in chuck 700. This is possible since bevelled section 214 and shallow recess 216 are both located at bottom end 213 of handle 210 and are only a small portion of handle 210. So while some sections of handle 210 do not have exactly the same diameter, the size of these sections relative to the other sections enables handle 210 to be firmly held by retention arms 700b.

Note that chuck 700 can even hold handle 210 in a secure manner such that instrument 200 rotates concentrically when only top gripping section 219 is in chuck 700. However, instrument 200 is not intended to be used for such large length variations as it is then necessary to measure the working length. Instrument 200 is preferably used for small variations in length, 1 mm to 3 mm, by extending only the sections at bottom end 213 of handle 210 out of chuck 700 which have 1 mm incremental lengths.

Handle 110' is an example of a handle that has a diameter and cross-sectional shape that are entirely uniform along its length. However, as indicated above, the entire handle does not need to have a uniform diameter and cross-sectional shape. Further, any handle that can be moved to a desired position and then be securely held once the handle means is positioned as desired within the chuck of the endodontic handpiece head such that the instrument can have a working length that can be varied based on the position of the handle means within the chuck of the endodontic handpiece head is within the scope of the present invention. For example, even though handle 22 is a latch-type handle it can be moved up and down within chuck 700 as handle 22 has a diameter and cross-sectional shape that are substantially uniform along a significant portion of its length. Note, however, that the latch at its top end is configured such that it cannot interfere with the ability to move handle 22 up and down within chuck 700. So while handle 22 does not have a diameter and cross-sectional shape which is the same along its entire length from its top end to its bottom end, the portion contacted by the retention arms 700b does have the same diameter and cross-sectional shape with the exception of the top end.

Even handle 12 provides enough surface area for chuck 700 to engage handle 12 in a latchless configuration through pressure exerted by the retention arms 700b. The ability to engage a handle such as handle 12 is further augmented when handle 12 is formed by a plastic material that provides greater friction than a metal handle, especially plastic materials that are deformable.

So the present invention enables any instrument to be used that has a handle shaped such as conventional handle 12 or conventional handle 22 as long as the handle can move up or down within a chuck of an endodontic handpiece head and be held at various positions in order to alter the working length of the instrument. Such instruments also preferably have incremental markings on either the handle or the file. Note that if an instrument is used with a conventional handle, the handle chamber of the chuck must have a greater depth than the length of the handle in order to recess the handle within the chuck.

FIG. 12 is an exploded perspective view like FIG. 11F which depicts retention arms 700b' of chuck 700' holding handle 410 of instrument 400. As shown in FIG. 12, retention arms 700b' are configured to mate with ridges 416 of handle 410. This mating configuration ensures that the working length is adjusted in discrete increments such as 1 mm until the top end of handle 410 encounters chuck base 700d'. Handle 410 can also be held in a chuck such as chuck 700 shown in FIGS. 11A–11E as the ridges provide sufficient surface area to engage with retention arms 700b in a secure manner. Similarly, handle 310 can be held in a chuck (not shown) having rounded extensions configured to extend into grooves 316 in a mated configurations or by a chuck such as chuck 700 as gripping sections 312 provide a large surface area for engagement with retention arms 700b. In summary, whether the handle has pointed ridges as shown in FIG. 12, sloped ridges, curved grooves, perpendicular recesses which partially encircle or fully encircle the handle, the retention arms can be flat or have a shape which corresponds with that of the handle in a mated configuration. It is however, preferable for the retention arms to grip the handle in a configuration such that the majority of the surface of the sidewall of the handle is in contact with the retention arms. Stated otherwise, the gripping sections of the handle are preferably at least half of the surface area of the handle other than its top and bottom surfaces.

As shown in FIG. 11A and FIG. 11C, head element 610 has a neck extension 612 which is coupled to neck element 620. Note that rim 614 of head element 610 is essentially coplanar with any bottom surfaces of head element 610. More particularly, rim 614 is essentially coplanar with the bottom surface of neck extension 612 and neck element 620. This essentially coplanar configuration is particularly useful since rim 614 is used as a stop as it is rested on the coronal surface of tooth 90.

The ability to use rim 614 as a stop is a significant advantage over conventional handpieces as it eliminates the need for rubber stoppers. Since rim 614 is immovable, use of the present invention provides a practitioner assurance that once the working length of the instrument is set there will be a secure stopping action to prevent insertion beyond the desired length and it will not change due to movement of a stop. The practitioner can also be assured that the working length of the instrument, the portion extending from chuck 700 beyond rim 614, is securely set once handle 110 is positioned in chuck 700.

Figures 1, 2:
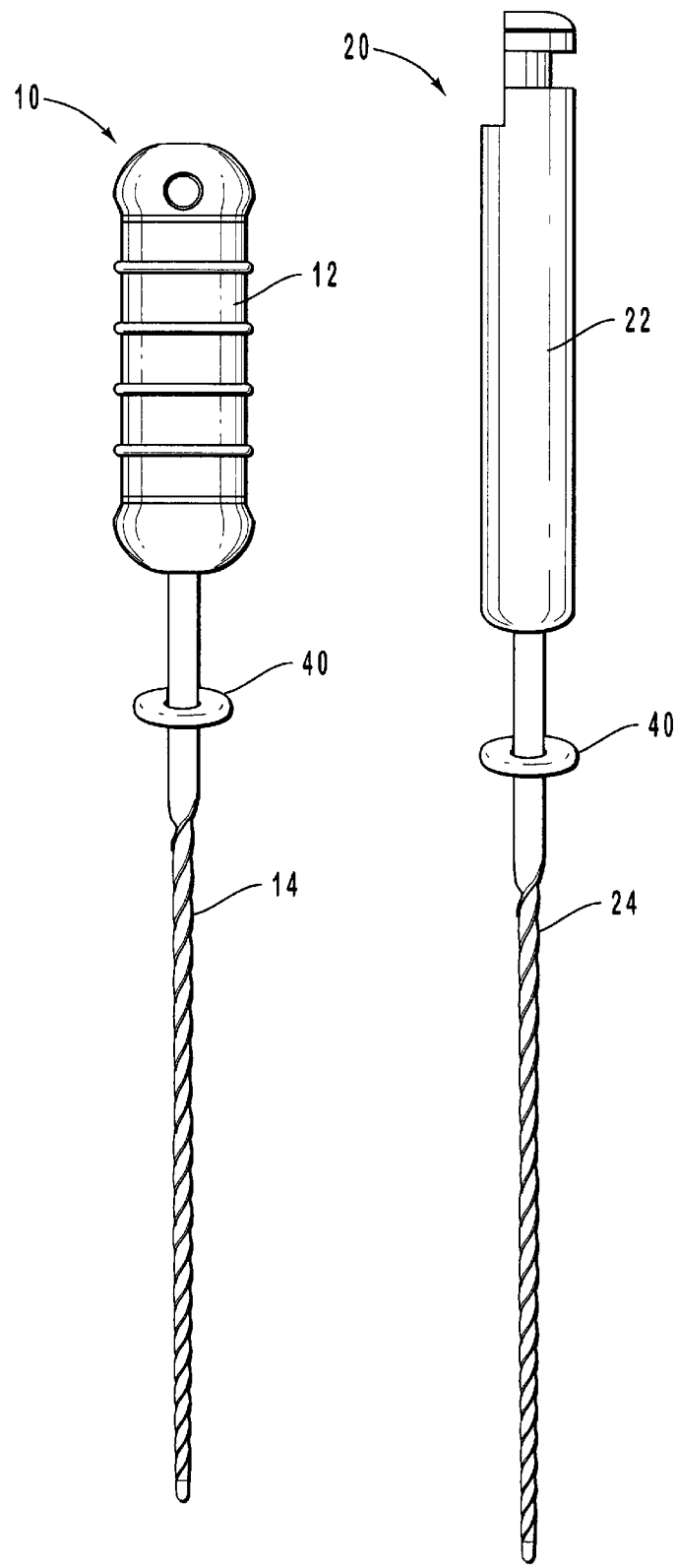
FIG. 1 is a perspective view of an instrument having a prior art peanut-shaped handle.
FIG. 2 is a perspective view of another instrument having a prior art latch-type handle.
Figure 3:
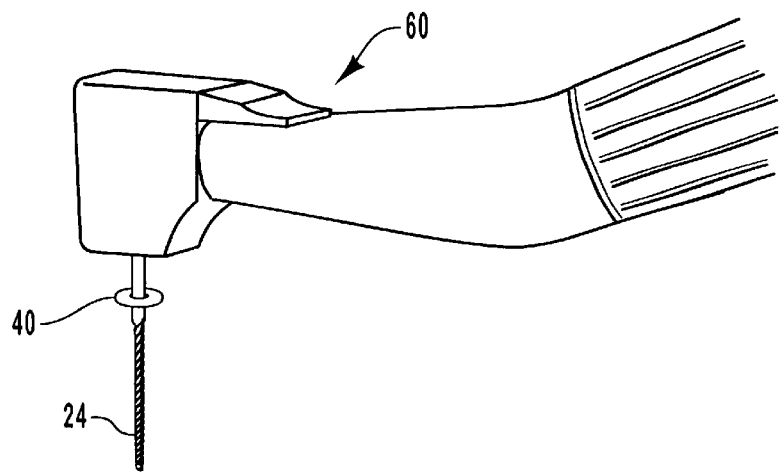
FIG. 3 is a perspective view of a head of an endodontic handpiece holding the instrument shown in FIG. 2.
Figure 4:
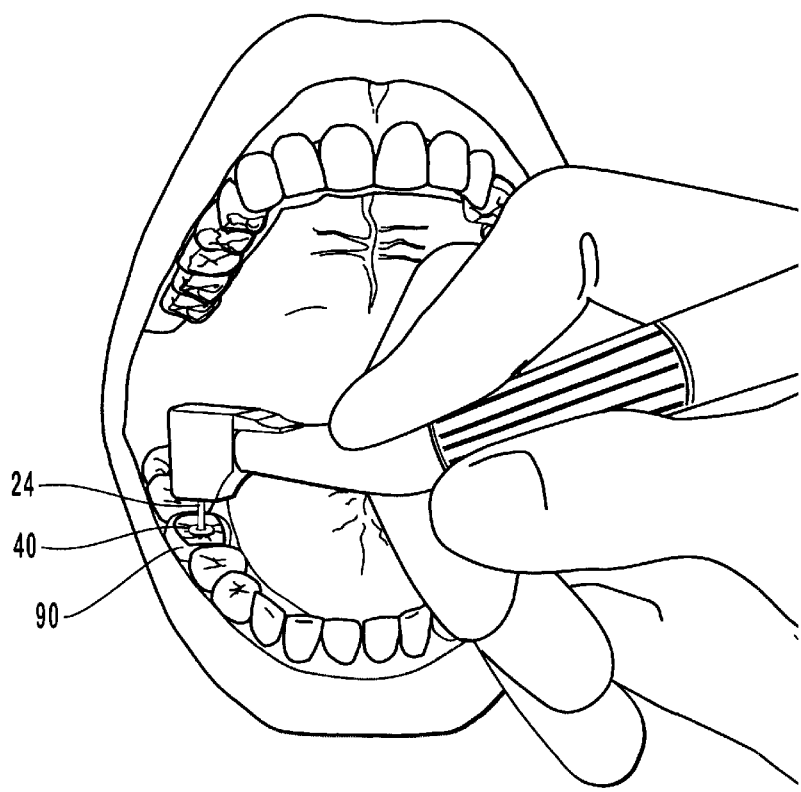
FIG. 4 is a perspective view of the endodontic handpiece shown in FIG. 3 being used in an endodontic procedure.

The essentially coplanar configuration enables a practitioner to easily identify the position of rim 614 relative to the coronal surface of the tooth since it is at least essentially the same as that of the larger neck element 620. Another advantage of this configuration is the reduced size of head element 610. While rim 614 can also be fully coplanar with neck extension 612 and neck element 620, there is preferably a slight differential or offset, such as 0.1 mm or 0.2 mm, as shown. Additionally, a head may be used which has a conventional configuration such as is shown in FIGS. 3–4 wherein the rim and the neck element have a more significant offset.

Figure 13A:
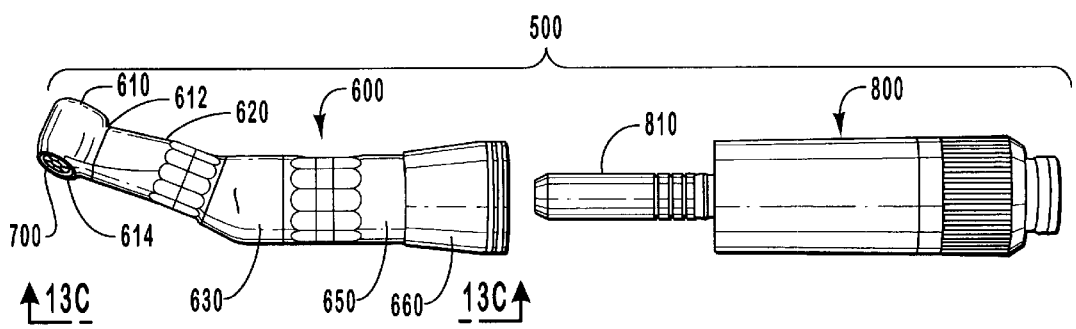
FIG. 13A is a perspective view of an endodontic handpiece including the head and the motor.
Figure 13B:
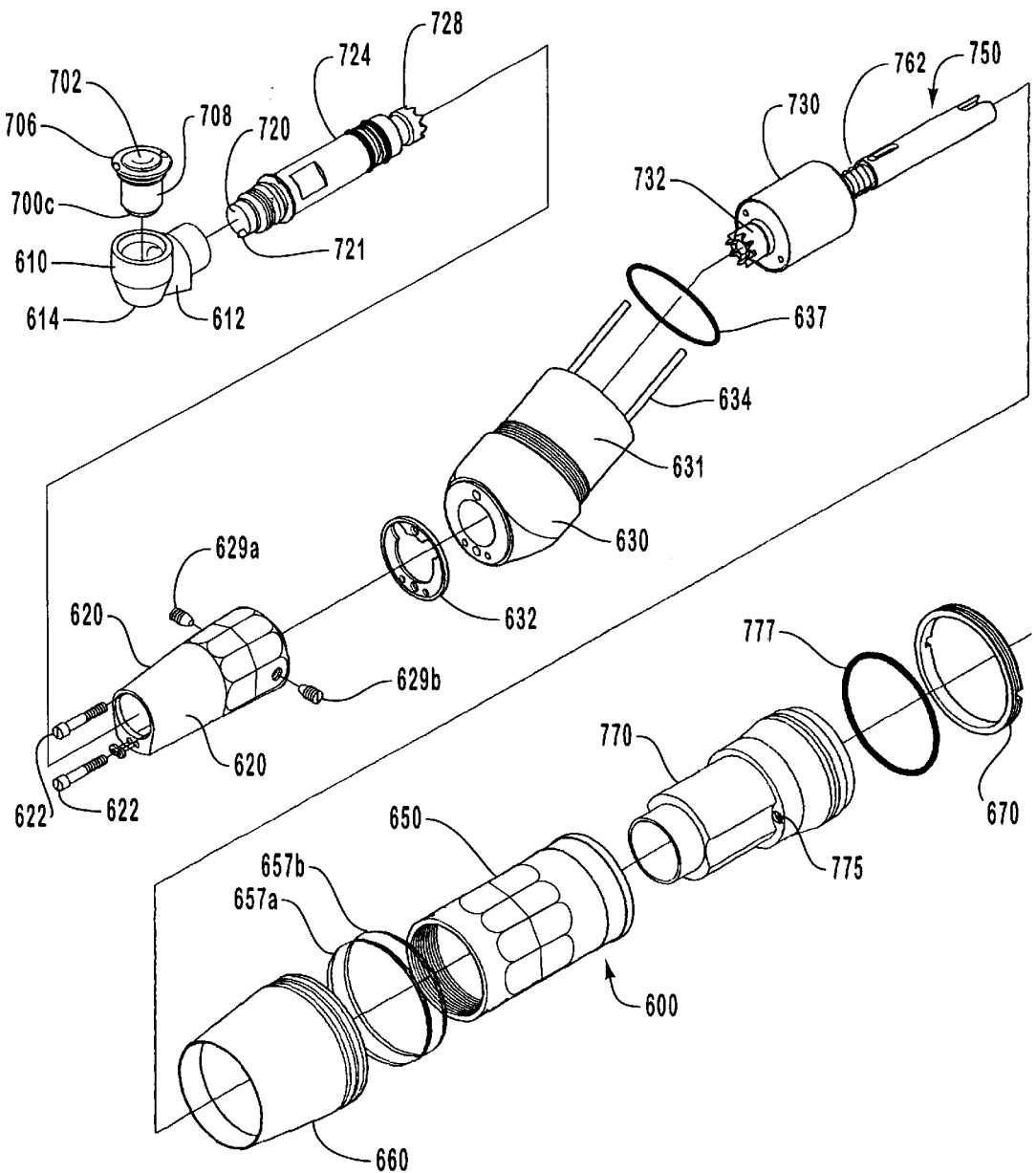
FIG. 13B is an exploded perspective view of the endodontic handpiece head shown in FIGS. 11A–11E and in FIG. 13A.
Figure 13C:
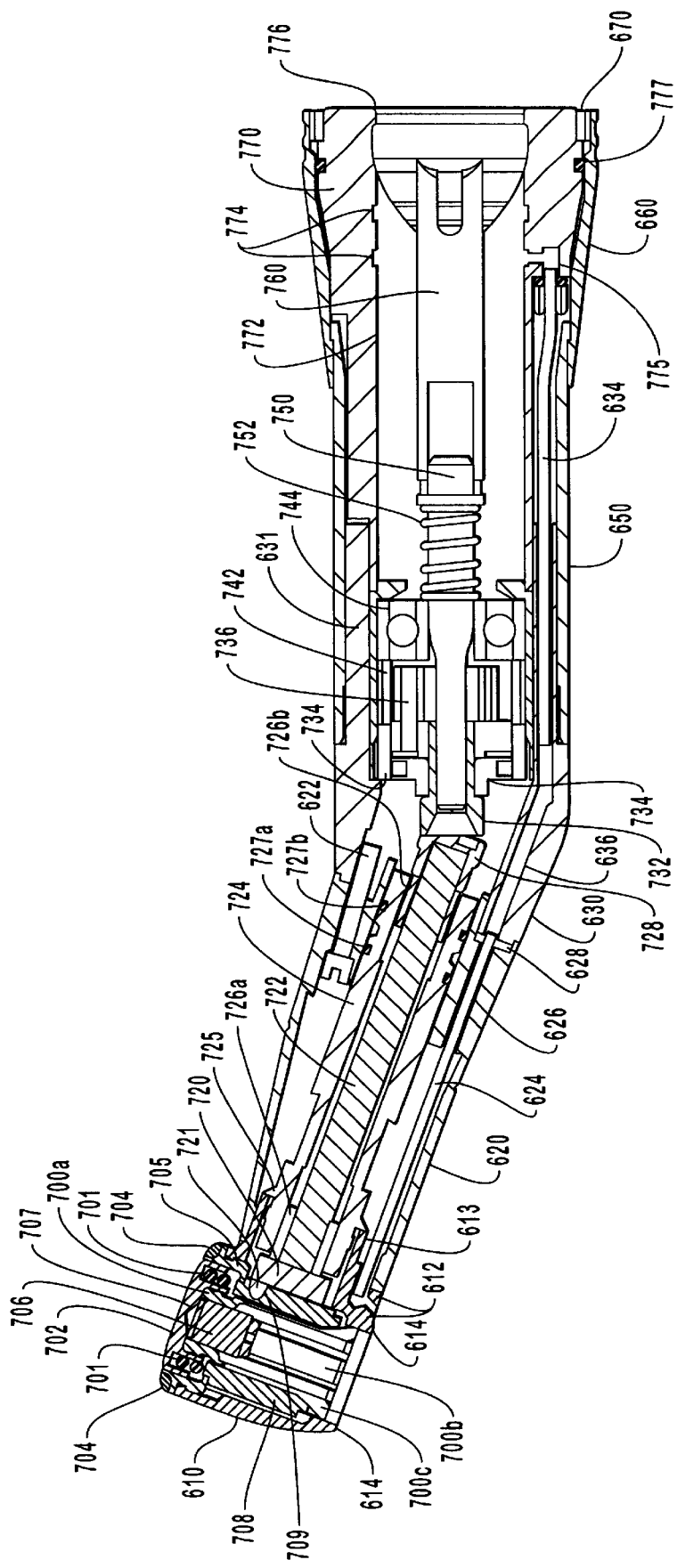
FIG. 13C is a cross-sectional view of the endodontic handpiece head shown in FIGS. 11A–11E and in FIGS. 13A–B.

Reference is now made to FIGS. 13A–13C to describe in detail the elements of head 600. FIG. 13A shows the exterior of the elements of head 600 as assembled and also motor 800. FIG. 13B is an exploded perspective view and FIG. 13C is a longitudinal cross-sectional view taken along cutting line 13C—13C of FIG. 13A.

While chuck 700 is shown having retention arms 700b which integrally extend from cylindrical portion 700a with spaces between each retention arm 700b, the chuck can have any suitable configuration. Alternatively, the retention arms can also be individual components which are not part of an integral cylindrical portion. In any event, the retention arms are configured to receive the handle of an endodontic instrument and to be pressed against the handle in a mated configuration such that the handle is firmly and concentrically held in varying positions relative to the chuck in order to vary the working length of the instrument, preferably by set increments. Chuck 700 and 700' are examples of chuck means for receiving and then releasably holding a handle.

A chuck spring 701 is positioned under cap 702 such that cap 702 is spring biased and pressure must be applied to depress cap 702. Cap ring 704 is positioned around cap 702. Depression of cap 702 enables the interior side of cap 702 to be urged against cylindrical portion 700a of chuck 700 and also against plug 706, via plate 707 on plug 706, which are located within cylindrical portion 700a Sleeve 708 prevents cap 702 from being further than is needed. Chuck spring 701 and cap 702 are an example of means for actuating the chuck such that the handle of an instrument may be received and released by the chuck.

Retention arms 700b of chuck 700 are slightly compressed together within chuck sleeve 708 such that they expand outward as shown in FIG. 11C when depressed as result of cap 702 being pushed. When cap 702 is released, spring 701 pulls chuck 700 upward such that flange portions 700c of retention arms 700b are moved away from rim 614 back inside head element 610 toward sleeve 708. Head element 610 is an example of a head element means for containing the chuck.

Chuck sleeve 708 has a movement receptacle 709 which is a depression configured to receive eccentric protuberance 721 of cam 720. Cam 720 reciprocates and transfers the reciprocating motion to chuck sleeve 708 and chuck 700 via the coupling of protuberance 721 in receptacle 709. The reciprocating motion of cam 720 therefore enables an instrument held in chuck 700 to be rotated in a reciprocating manner. The range of motion being about 30°. The combination of receptacle 709 in chuck sleeve 708 and protuberance 721 of cam 720 provides an examples of means for rotating the chuck. The chuck rotating means may also include the other components as described herein which rotate cam 720 such as cam shaft 722 and other connected components. Neck element 620 is an example of housing means for supporting the chuck rotating means. The housing means may include other external elements of head 600 as described hereinbelow which house or support the chuck rotating means such as elbow element 630, sheath element 650, and cone sleeve element 660 as well as a component which is primarily an internal component such as ferrule 770.

As noted above, cam 720 is coupled to cam shaft 722. Cam shaft extends within bearing sheath 724. A gear 728 is located on cam shaft 722 opposite cam 720. Cam 720 and gear 728 extend beyond bearing sheath 724 such that cam shaft 722 is only shown in the cross-sectional view of FIG. 13C. Bearing sheath 724 has a flange 725 which extends radially outward and is positioned in contact with sheath engagement portion 613 of neck extension 612. Cam shaft 722 rotates against bearings 726a and 726b which are located at the opposing ends of cam shaft 722. O-rings 727a and 727b are positioned around bearing sheath 724.

Neck element 620 is coupled to elbow element 630 by a screw 622. A member 624 extends within the chamber defined by neck element 620 and into a channel 626. Elbow element 630 also has a channel 636 which is aligned with channel 626. A pin 628 is positioned through member 624 at the juncture of channel 626 and channel 636 such that member 624 barely extends into channel 636 as shown in FIG. 13C. Screws 629a and 629b also extend into neck element 620. Sealing washer 632 shown in FIG. 13B is not shown in FIG. 13C.

Gear 728 engages gear 732 of planetary gear carrier 734. Planetary gear carrier 734 is shown in FIG. 13C but is hidden in FIG. 13B by bearing sheath 730. Planetary gear carrier 734 has a large gear 736 which is engaged by a ring gear identified in FIG. 13C at 742. Planetary gear 734 transmit rotation, at a ratio of 4:1, to ring gear 742.

As shown in FIG. 13C, a long face pinion 750 extends into planetary gear carrier 734 and rotates within ball bearing 744. As shown in FIG. 13B and FIG. 13C, the other end of pinion 750 extends into shaft 760 with a spring 752 positioned to be compressed between ball bearing 744 and shaft 760.

Shaft 760 extends within a receiving chamber 662 defined by ferrule 770. Chamber 772 has slots 774 and an opening 776. Chamber 772 and opening 776 are configured to receive drive shaft 810 of motor 800 which is configured to engage shaft 760.

Elbow element 630 has a sheath portion 631 which is coupled within sheath element 650. Note that members 634 extend from channel 636 of elbow element 630 and are engaged by receptacle 775 of ferrule 770.

Cone sleeve element 660 fits over sheath element 650 in an interlocking manner as shown in FIG. 13C. Cone sleeve element 660 also fits over ferrule 770. Positioned between cone sleeve element 660 and ferrule 770 are o-ring 777 and threaded ring 670. Note that o-rings 657a and 657b shown in FIG. 13B are not shown in FIG. 13C.

In addition to the endodontic handpiece head or contra-angle shown at 600 and as described above, other contra-angles may have similar features. Examples of suitable contra-angles include those sold by DynaDent as 24641, those sold by KaVo as 3LD or as 53LDN, those sold by Kerr as M4, those sold by Micromega as 6/15AE, those sold by MTI as LX-EF and those sold by NSK as TEP-E10R, TEQ-E10R, IS-35 and IS-40.

Examples of patents which disclose various designs for chucks and handpieces in general include U.S. Pat. No. 3,646,677 entitled Collet Chuck for a Dental Instrument; U.S. Pat. No. 4,536,157 entitled Lever Actuated Chuck Mechanism for Dental Handpiece; U.S. Pat. No. 4,595,363 entitled Dental Handpiece Having Means for Opening and Closing a Chuck; U.S. Pat. No. 4,611,990 entitled Dental Handpiece Construction; U.S. Pat. No. 4,661,062 entitled Dental Handpiece Contra-Angle Head; U.S. Pat. No. 4,874,314 entitled Socket to Clampingly Hold Dental Tools; U.S. Pat. No. 5,090,906 entitled Push-Button Control Device for a Dental Instrument and European Patent No. D 281 847 B1. These patents are all incorporated by reference.

In addition to the above patents the following patents which are owned by NSK of Japan are also incorporated by reference. These patents include: U.S. Pat. No. 5,857,851 entitled Dental Handpiece; U.S. Pat. No. 5,807,108 entitled Dental Handpiece; U.S. Pat. No. 5,718,582 entitled Dental Tool Chuck; U.S. Pat. No. 5,688,122 entitled Chucking Device for a Dental Tool; U.S. Pat. No. 5,575,648 entitled Dental Turbine Spindle Assembly; U.S. Pat. No. 5,567,154 entitled Dental Turbine Drive Having Means for Automatic Speed Control; U.S. Pat. No. 5,476,380 entitled Dental Handpiece; U.S. Pat. No. 5,425,638 entitled Turbine for a Dental Handpiece; U.S. Pat. No. 5,423,678 entitled Handpiece Having Bearing Protective Member; U.S. Pat. No. 5,340,311 entitled Dental Handpiece; U.S. Pat. No. 5,312,252 entitled Turbine for a Dental Handpiece; U.S. Pat. No. 5,275,558 entitled Dental Handpiece, Bur Mount Operating System; U.S. Pat. No. 5,057,015 entitled Dental Handpiece Having an Arrangement to Form Compatible Connections to Differently Designed Rotatable Joints; U.S. Pat. No. 5,040,980 entitled Dental Handpiece With Spring Grip Chuck and Lever Release Mechanism; U.S. Pat. No. 4,973,247 entitled Dental Handpiece Assembly, U.S. Pat. No. 4,921,424 entitled Dental Handpiece; U.S. Pat. No. 4,786,251 entitled Dental Handpiece and High Speed Turbine Assembly; U.S. Pat. No. 4,690,641 entitled Contra-angle or Turbine Head of a Dental Handpiece; U.S. Pat. No. 4,642,051 entitled Dental Handpiece; and U.S. Pat. No. 4,595,363 entitled Dental Handpiece Having Means for Opening and Closing a Chuck.

Note that the endodontic handpieces disclosed herein are all examples of endodontic handpiece head means for releasably holding a handle means of an endodontic instrument and for simultaneously rotating the endodontic instrument. Additionally, endodontic handpiece heads which are adapted such as handpiece head 600 as described above to enable the rim around the chuck to act as a stop are endodontic handpiece head means for releasably holding a handle means of an endodontic instrument and for simultaneously rotating the endodontic instrument while also acting as a stop to prevent the endodontic instrument from being inserted into a root canal beyond its working length.

The endodontic instruments disclosed herein as having a handle configured within the scope of the present invention can have any suitable file. While conventional files may be utilized and the instruments may be utilized in accordance with conventional methodologies, the instruments preferably have files which are specifically adapted for cleaning the upper portions of a root canal without cleaning the apical portion. Such instruments and related methods are disclosed in U.S. patent application Ser. No. 09/536,284 entitled Abrasive Coated Endodontic Instruments and Related Systems and Methods for the Anatomical, Sectional and Progressive Corono-Apical Preparation of Root Canals which was filed on Mar. 27, 2000 for Francesco Riitano and Dan E. Fischer. Ser. No. 09/536,284 is a continuation-in-part of U.S. patent application Ser. No. 09/492,566 entitled Endodontic Systems and Methods for the Anatomical, Sectional and Progressive Corono-Apical Preparation of Root Canals with Minimal Apical Intrusion which was filed on Jan. 27, 2000 for Francesco Riitano and Dan E. Fischer. Ser. No. 09/492,566 is a continuation-in-part of U.S. Pat. No. 6,059,572 entitled Endodontic Methods for the Anatomical, Sectional and Progressive Corono-Apical Preparation of Root Canals with Three Sets of Dedicated Instruments issued to Francesco Riitano. Ser. No. 09/492,566 is also a continuation-in-part of U.S. Pat. No. 6,045,363 entitled Endodontic Methods for Progressively, Sectionally and Anatomically Preparing Root Canals with Specific Instruments for each Section having Predetermined Working Lengths issued to Francesco Riitano. These patents claim priority through two U.S. patents issued to Francesco Riitano including U.S. Pat. No. 5,775,904 and U.S. Pat. No. 5,642,998 which are both entitled Endodontic Instrument for Rapid Widening of the Canal Mouth and Specific Rectification of the First Two-Thirds to Italian Patent Application No. RM95A000377, which was filed on Jun. 6, 1995. For purposes of disclosure of the present invention, each of the foregoing applications and patents is incorporated herein by specific reference.

The systems and methods of endodontic instruments disclosed in Ser. No. 09/536,284 essentially involve sequentially cleaning a root canal in sections from the crown to the apex by dividing it into three sections including an operative coronal portion, an operative middle portion and an apical portion. An operative phase generally corresponds with the particular sections or portions of the operative root canal and specific instrumentation is used in each phase. An overview of the methodology is provided hereinbelow; however, the cleaning of the root canal up to the apical portion is the phase which is most related to the present invention.

Before describing the methodology, it is necessary to set forth the divisions of the operative root canal as shown in FIG. 14A. During root canal therapy, the operative root canal is considered to include the anatomical root canal, which extends from the pulp chamber or the floor 956 of the pulp chamber 946 to the apex 954, and the operative coronal portion 960 thereabove. More specifically, the operative root canal comprises the operative coronal portion 960, the operative middle portion 962 and the apical portion 964. Operative coronal portion 960 essentially includes the access cavity walls. The operative middle portion 962 is the upper portion of the anatomical root canal while the apical portion 964 is the lower portion of the anatomical root canal.

The divisions of the operative root canal are distinguished from the nomenclature of the anatomical root canal as used to designate the sections before opening the tooth wherein the anatomical root canal is divided into the apical portion and the coronal portion. The coronal portion of the anatomical root portion is conventionally defined as the upper portion of the anatomical root canal which terminates at the floor of the pulp chamber. However, once the pulp chamber is exposed and instruments are introduced into the root canal, the opening into the tooth should be treated as an extension of the operative root canal as it is then a continuous chamber or open tract. Accordingly, the access walls are considered part of the operative root canal and are designated as the operative coronal portion or the access portion.

Apical portion 964 extends from the apex of root canal 952 up to an area of anatomical root canal 952, such that the length of the apical portion is less than half of the length of the anatomical root canal as measured from the apex to floor 956. Apical portion 964 is accordingly generally the bottom one-half to one-third of the anatomical root canal 952. The actual length of the apical portion varies depending on many factors such as the type of tooth and the age of the tooth. However, the apical portion typically has a length in a range from about 3 mm to about 4 mm as measured from the apex.

As also indicated hereinabove, operative middle portion 962 is the top portion of the anatomical root canal 952 and extends from floor 956 down to an area of anatomical root canal 952, such that the length of the operative middle portion is greater than half of the length of anatomical root canal 952. More specifically, operative middle portion 962 is generally the top two-thirds of anatomical root canal 952 as measured down from floor 956. The length of operative middle portion can be estimated by identifying the overall length of the root canal, typically by use of radiography, and then subtracting about 3 mm to about 4 mm from the overall length.

As previously indicated, the three sections are treated in primarily distinct sequential phases. These phases include: preparation of the operative coronal portion, cleaning or preparation of the operative middle portion, and finally cleaning of the apical portion. Additionally, access into the apical root portion is preferably improved before the apical portion is cleaned.

FIG. 14A depicts the upper portions of root canal 952a of tooth 940 being cleaned with instrument 100 after several steps in the methodology have been achieved as described hereinbelow. The first phase or coronal phase involves exposing the pulp chamber and also preferably other steps to enhance accessibility into operative middle portion 962 and also apical portion 964. Accordingly, the coronal or access phase is initiated by exposing pulp chamber 946 through removing the top of the chamber. More particularly, the overhanging portions of enamel 942 and dentin 944 are first removed. Once pulp chamber 946 has been exposed, the pulp material 950 contained therein is removed. At this point, pulp material 950 still extends within root canal 952 from apices 954a and 954b to the floor 956 of pulp chamber 946.

After an opening is formed into the tooth to provide access into the root canal during the first phase, it is preferable to remove or reduce dentinal or enamel protrusions or irregularities that may obscure or hinder access of instruments into the remaining portions of the operative root canal. For example, dentinal shelves as shown at 966 depicted in FIG. 14A are preferably reduced or rectified to provide greater access for instrumentation during the subsequent phases. More particularly, interferences are preferably removed or minimized such that instruments can be inserted in the anatomical root canal in a relatively straight manner. Accordingly, FIG. 14A depicts file 130 inserted into root canal 952a with the dentinal shelf removed thereabove and as not being yet removed above the other canal, 952b. Rectification or regularization can be achieved by any suitable means. Example of means for rectifying dentinal shelves are set forth in U.S. Pat. No. 5,642,998 and U.S. Pat. No. 5,775,904 which were incorporated by reference hereinabove. It may also be necessary to widen the tract of the operative coronal root canal.

Once the operative coronal portion has been adequately prepared, it is preferable to prepare an x-ray image of the tooth to identify the length of the operative root canal in order to determine the preferred working length for the instrument or set of instruments to be used in the next phase. The preferred working length is preferably identified by subtracting about 3 mm from the total radiographic length of the operative root canal. The total radiographic length is preferably derived from a radiograph made using a localizator and a long cone radiographic head.

The second phase involves cleaning or preparation of operative middle portion 962. It may also involve to some extent further rectification of the operative coronal or access portion 960 through further removal of any ledges or outcroppings which prevent straight and easy access into the operative middle portion 962. Additionally, it may also involve some degree of rectification of the upper region of operative middle portion 962.

The length of each file in the set used to clean the operative middle portion depends on the length of the tooth being cleaned. More particularly, after identifying the length of the root canal from an x-ray image, the length of the file to be used in the operative middle portion is determined by subtracting 3 mm from this identified length of the root canal. This length is typically between about 15 and about 20 mm, however, longer files, such as a 25 mm long file, are typically required for canine teeth. To provide for the different root canal configurations which may be encountered, it is preferred to have files with lengths ranging from about 8 mm to about 35 mm. However, files with lengths ranging from about 10 mm to about 30 mm will be most utilized and files with lengths ranging from about 14 mm to about 26 mm will be the most frequently utilized.

After identifying the combined length of the operative middle portion and the operative coronal portion and after removing the overhanging enamel 942 and dentin 944, the practitioner selects an instrument or a set of instruments with a file length which approximately corresponds with the combined length of the operative middle portion length and the operative coronal portion. Handle 110 of instrument 100 is then positioned within chuck 700 and is locked into place once the position of handle 110 relative to chuck 700 is such that the working length of instrument 100 corresponds with the combined length of the operative middle portion and the operative coronal portion of the root canal. Handpiece 500 can then be used to rotate instrument 100 as shown. As indicated above, instrument 100 is preferably rotated in a reciprocating motion such that instrument 100 rotates for example, clockwise for half of a revolution and then counterclockwise for half a revolution. A reciprocating motion is preferred as such motion enables the file to alternately engage material 950 and the walls of the operative middle portion of the root canal in a manner that removes material 950 and to then rotate in the opposite direction such that the file 130 less aggressively engages material 950 and the operative middle portion walls, depending on the file design. Accordingly, rotating instrument 100 in a reciprocating motion minimizes breakage of file 130 when file 130 encounters a surface that prevents rotation of instrument 100 in a direction that enables cleaning and removal of material 950. Instrument 100 may, however, also be continuously rotated in one direction only or be vibrated.

As shown in FIG. 14A, file 130 is inserted into root canal 952*a* down through operative middle portion 962 without extending substantially into apical portion 964. By limiting the working length of instrument 100 such that it cannot significantly extend into apical portion 964 once positioned in chuck 700, a practitioner can aggressively clean the operative middle portion without worrying that the instrument will overly thin the root canal, perforate the apex or that cleaning will cause extrusion of material through the apex. Another benefit of cleaning the operative middle portion first is that the apical portion is then generally more accessible and easily cleaned. Additionally, since instruments are selected for use in cleaning the operative middle portion which have files lengths that do not permit entry into the apical portion once properly positioned within a chuck of a handpiece such as handpiece 500, the likelihood of jamming or breaking a tip of an instrument while working in the confined space of the apical portion is prevented.

Figure 14B:
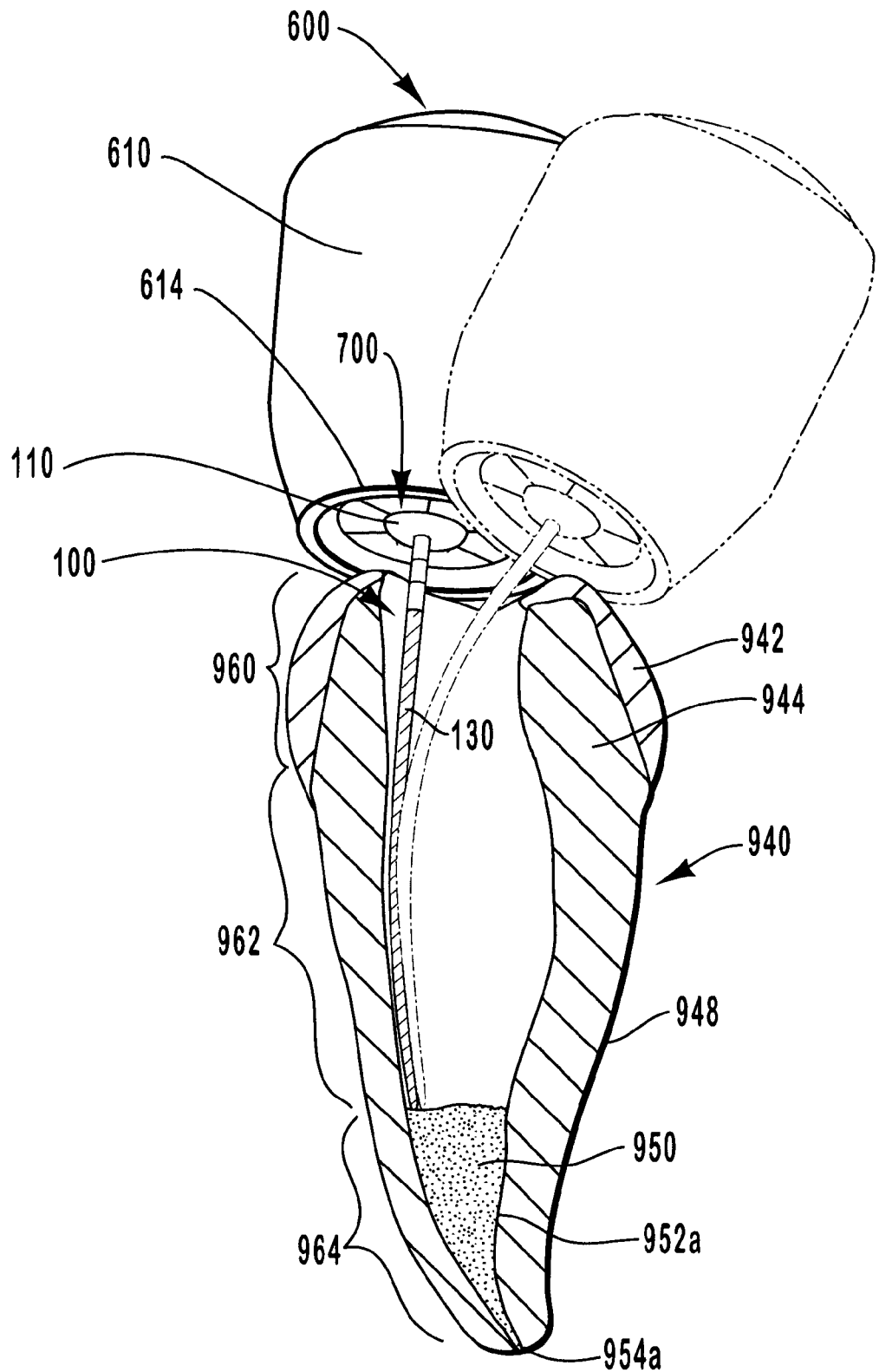
FIG. 14B is a longitudinal cross-sectional view of the tooth shown in FIG. 14A taken along cutting line 14B—14B to depict the cleaning of the pulp material from the operative middle portion of the root canal with instrument 100.

By instrumenting in the operative middle portion and the operative coronal portion before the cleaning the apical portion, the practitioner can use an instrument that is relatively flexible compared to the conventional instruments. As shown in FIG. 14B, which is a cross-sectional view taken along cutting line 14B—14B of tooth 940 in FIG. 14A, file 130 is sufficiently flexible to be flexed or curved against any surface of operative middle portion 962 or operative coronal portion 960 and yet is sufficiently rigid to remain flexed against the surface during a cleaning motion such as a longitudinal motion, a rotational motion or a reciprocating rotational motion. The file is also sufficiently resilient that substantial deformation of the file does not occur due to the forces experienced during cleaning of the pulp material from the root canal. The files are designed to have such flexibility and rigidity by properly selecting a combination of factors including the diameters of the files at the proximal or top ends and at the tips as well as the material used to form the files.

Instrument 100 is shown in FIGS. 14A and 14B being moved in a longitudinal movement or up and down movement as well as being rotated while file 130 is flexed or arched to urge the file against the root canal surfaces. As shown, the configuration of the files used to clean the operative middle portion, and preferably the operative coronal portion as well, enable a practitioner to move the files around the perimeter or from side to side to contact the perimeter. More particularly, the files are pushed against the surfaces of the root canal and simultaneously moved around the perimeter or periphery of the root canal until the practitioner has reached the beginning location of the cleaning and shaping process.

Since the file is moved around the perimeter, the file has more than one center of motion during cleaning of the operative middle portion of the root canal, such as a pivot point or center of rotation, as the tip of the file or at least a part of the abrading portion does not generally remain primarily in one position. This is in sharp contrast to prior art methods which limited the practitioner to essentially rotating a conically shaped file to yield a cone shaped borehole. Such prior art methods yield a final anatomy that is dictated by the shape of the instrument. More particularly, prior art methods result in an anatomy with a significant footprint from the instrument, which is a borehole that obviously corresponds to the shape of the file, without even cleaning all of the perimeter of the root canal. In addition to failing to fully clean the root canal, the tooth can be overly thinned, perforations may result or the tooth may be unnecessarily weakened when cleaned by such prior art methods.

The contours of the operative coronal portion and the operative middle portion can be used during their cleaning by a practitioner as a guide for the movements of the files due to the properties of the files such as flexibility, rigidity and limited working length. As a result of the ability to move the file by following the contours of the operative middle portion during cleaning and shaping, the original anatomy of the root canal is substantially maintained despite the cleaning of essentially all pulp material from the operative middle portion. For example, when the original perimeter is, generally elliptical, the files can be urged along one side and then along the next side wall in a manner such that the resulting cleaned and shaped root canal has a perimeter that is still generally elliptical. Similarly, if the original shape of the perimeter of a root canal as seen from a transverse cross-sectional view, is generally circular, laminar or tear shaped, then the cleaned and shaped walls will also be generally circular or tear shaped. In other words, the original anatomy of the root-canal controls the shape of the resulting cleaned and shaped anatomy due to this methodology. The understanding that the final anatomy is guided by the shape of the original anatomy enables a practitioner to more confidently urge a file such as file 130 against all surfaces of a root canal and aggressively clean all of the surfaces of the operative middle portion of the root canal since the likelihood of overly thinning the root canal or causing lateral perforations is diminished.

As indicated above, the ability of instruments having such files to clean the operative middle portion of a root canal is enhanced when the instruments also have handles configured for incremental adjustment and are used in combination with an appropriate handpiece. Benefits are described in detail hereinbelow of using such instruments together with a handpiece which has a chuck configured to hold an incrementally adjustable handle in a mated configuration and a rim around the chuck.

One of these benefits is the secure stopping action provided by a rim such as rim 614. As set forth above, rim 614 is not movable so the practitioner is assured that once the working length of the instrument is set there will be a secure stopping action to prevent insertion beyond the desired length and it will not change due to movement as may occur with conventional stoppers such as stopper 40. While such a rim is useful with conventional root canal therapy techniques, it is particularly useful for cleaning the operative middle portion in the systems and methodology described above. Conventional endodontic techniques generally involve the mere rotation of a set of instruments of increasing size in one location. Such motion presents less opportunities for a stopper to be dislodged when compared with cleaning the operative middle portion by following the contours of the root canal while flexing the file against the root canal surfaces. More particularly, the cleaning movements required to follow root canal contours while flexing the instrument is much more aggressively oriented than conventional techniques so the secure stopping action provided by rim 614 enhances the ability to use such a methodology as a practitioner is assured of the safety of the methodology. Note that although the movements may be more aggressive, the results of the methodology are much less aggressive in terms of the removal of dentin compared with conventional techniques.

Figure 14C:
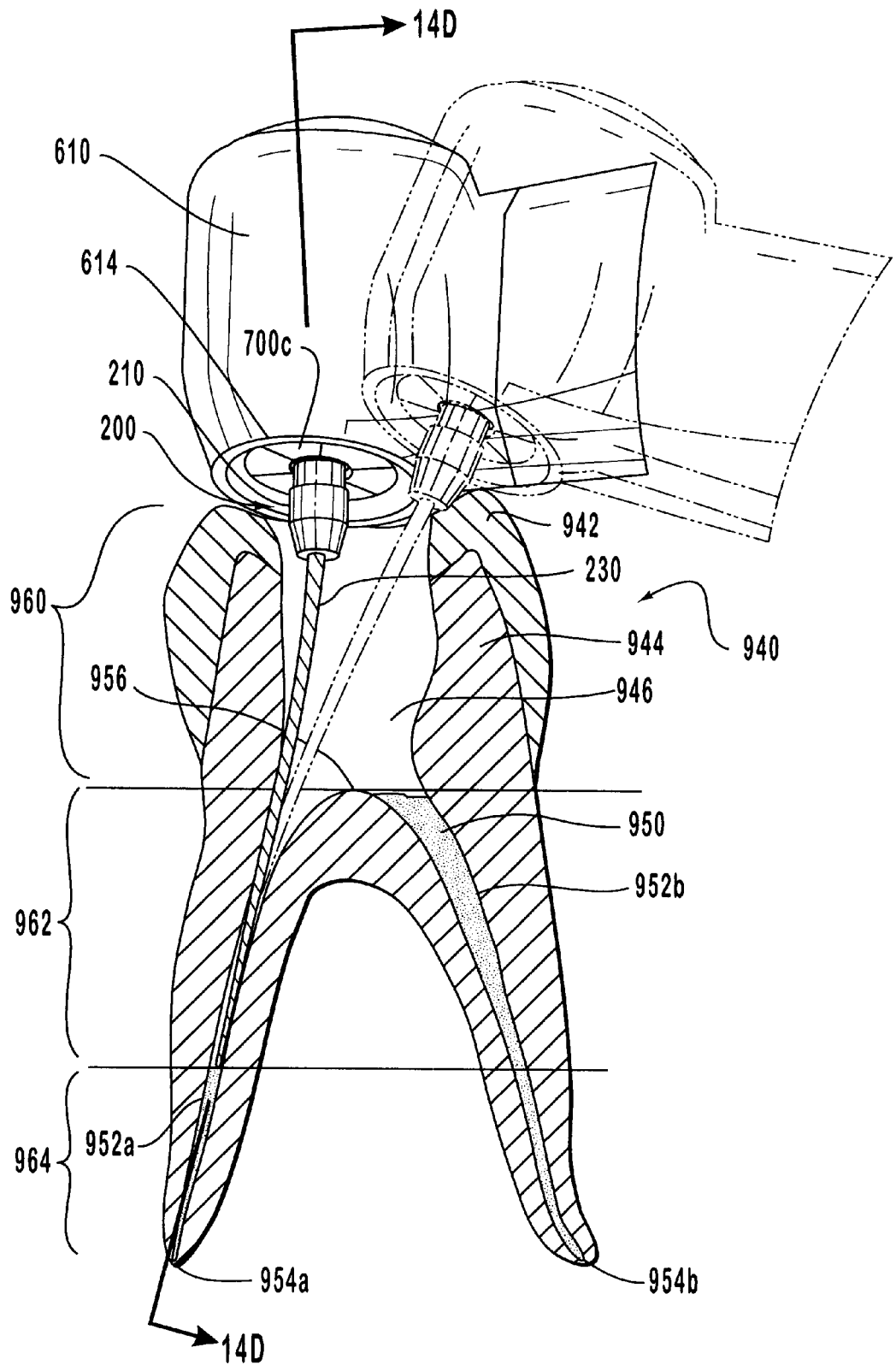
FIG. 14C is a longitudinal cross-sectional view of a tooth with a file portion of a file instrument 200 inserted into the root canal up to the apical portion.
Figure 14D:
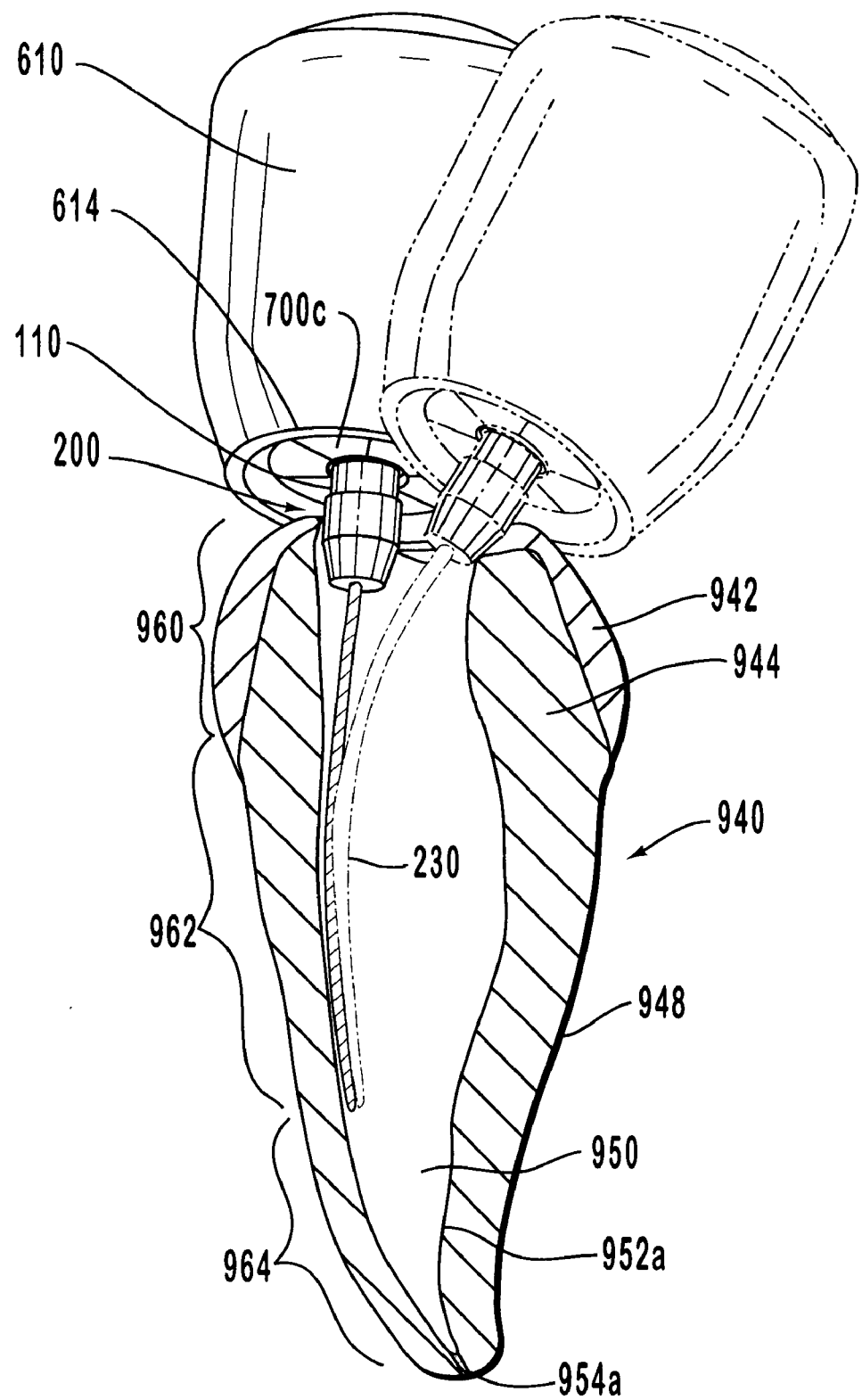
FIG. 14D is a longitudinal cross-sectional view of the tooth shown in FIG. 14A taken along cutting line 14C—14C to depict the cleaning of the pulp material from the operative middle portion of the root canal with instrument 200.

FIG. 14C and FIG. 14D depict instrument 200 being used with handpiece 500 in accordance with the methodology described above. Rim 614 is shown providing a secure stopping action. However, handle 210 extends into the root canal instead of being recessed like handle 110. In general, it is preferred to have the handle recessed as a recessed handle does not interfere with the movement of the file and the instrument has a greater range of motion. Since a handle such as handle 210 has a much larger diameter than file 230, it is more difficult to maneuver the instrument when the handle extends into the narrow root canal opening.

Many practitioners use several standard length instruments such as those having a length of 21 mm or 25 mm and then adjust the length through the use of stoppers. Some practitioners, however, prefer to avoid the use of rubber stoppers by using endodontic systems with sets of instruments having as many different lengths as are needed to clean root canals by conventional techniques. For example, a system may be sold wherein instruments have incrementally different lengths such as 21 mm, 22 mm, 23 mm, 24 mm and 25 mm, thereby eliminating the need for stoppers in this range. Due to the aggressive movements involved in cleaning the operative middle portion, as described above, without the use of instruments having handles adapted for incremental adjustment and a corresponding handpiece head, some practitioners might be more inclined to rely on a system of such instruments having incrementally different lengths. However, as the above discussion indicates, such a need is eliminated through the use of instruments having handles configured for incremental adjustment. Accordingly, less instruments are required to have a complete system since the working length of the instrument is adjustable by adjusting its position within a mated chuck by 1–3 mm or more. A practitioner can confidently expect to clean all operative middle portions of root canals, in accordance with the methodology discussed above, with only a limited system of endodontic instruments or sets of instruments. This is an additional benefit of the use of instruments having handles adapted for incremental adjustment and having filed configured for cleaning the operative middle portion of a root canal in combination with an endodontic handpiece head having a chuck which mates with the handle.

Files used to clean the operative middle portion in accordance with the methodology disclosed herein, may be configured to abrade along nearly their entire length as shown in FIG. 14A and FIG. 14B or along their entire length as shown in FIG. 14C and FIG. 14D. An advantage of having nearly all or all of the portion of a file extending from a handle configured for abrading is that the file can simultaneously abrade both operative coronal portion 960 and operative middle portion 962. A primary benefit of simultaneously abrading both portions is the ability to further straighten the operative coronal portion while cleaning the operative middle portion.

FIGS. 14C–14D depict instrument 200 being used to clean 940 as it is moved by chuck 700 of handpiece head 600. As discussed above, file 230 differs from file 130 in that file 230 does not have a shank portion extending from the handle. A file such as file 230 is especially useful when it is necessary to adjust the working length such that handle 210 extends significantly into pulp chamber 946. A handle that extends significantly into pulp chamber 946 like handle 210 does in FIGS. 14C–14D cannot abrade so it is necessary for the entire length of the file to be adapted for abrading to ensure that it can abrade along the upper portion of the root canal. While such a file may be advantageous in some circumstances, it is generally preferable to use an instrument that enables the handle to be fully positioned in the chuck as shown in FIGS. 14A–14B so that the handle does not potentially interfere with the movement of the file and the handpiece.

In contrast to being adapted to abrade along their entire length or nearly their entire length, a file of a conventional instrument typically has a smooth shank portion on a large portion of its proximal end and an abrading portion which extends therefrom to its distal insertion end. Such shank portions are often about one-third of the overall length of the portion of the file extending from the handle. ISO standardized files have abrading portions of up to 16 mm and the remainder of the file is a smooth shank portion. Such conventional files frequently fail to remove interferences extending from the access or root chamber above the anatomical root canal so the instruments must bend around the interferences, thereby further increasing the likelihood of wall perforations, overthinning and failing to clean significant portions of the canal. It especially increases the likelihood of iatrogenic modifications resulting from the tip of the file.

Removal of pulp material 950 from operative middle portion 962 removes the majority of bacteria in the pulp canal since the majority of bacteria in an infected root canal is typically located in the operative middle portion. Not only is the greatest volume of bacteria in the operative middle portion but it is also believed that the concentration is greater in the operative middle portion. Since a certain minimum threshold must generally be reached for complications to arise due to microbial presence in a root canal, removal of the pulp material in the operative middle portion significantly reduces the likelihood of such complications.

By removing the majority of bacteria before cleaning the apical portion there is also less likelihood of exposing the surrounding tissue to bacteria due to overly thinning the root canal, perforation or extrusion of material from the canal. The greatest likelihood for the occurrence of complications such as over thinning of root canal walls, perforation or extrusion of material from the canal is in the apical portion. The apical portion is the most likely site for such complications as apical portions are more complex and delicate compared the operative middle portions of teeth. Since such complications are most likely to occur in the apical portion, it is highly beneficial to have the material removed from the operative middle portion in order to minimize the amount of material that can come out of the root canal to cause problems. For example, in the event of an apical extrusion far less septic material may be expressed during instrumentation in accordance with present methodology than if the apical extrusion occurred as a result of cleaning in accordance with conventional methods wherein files are inserted to the apical portion before cleaning the operative middle portion. As a result, removal of the majority of bacteria before cleaning the apical portion increases the likelihood of successful root canal therapy in several ways compared with conventional methods.

Figure 15:
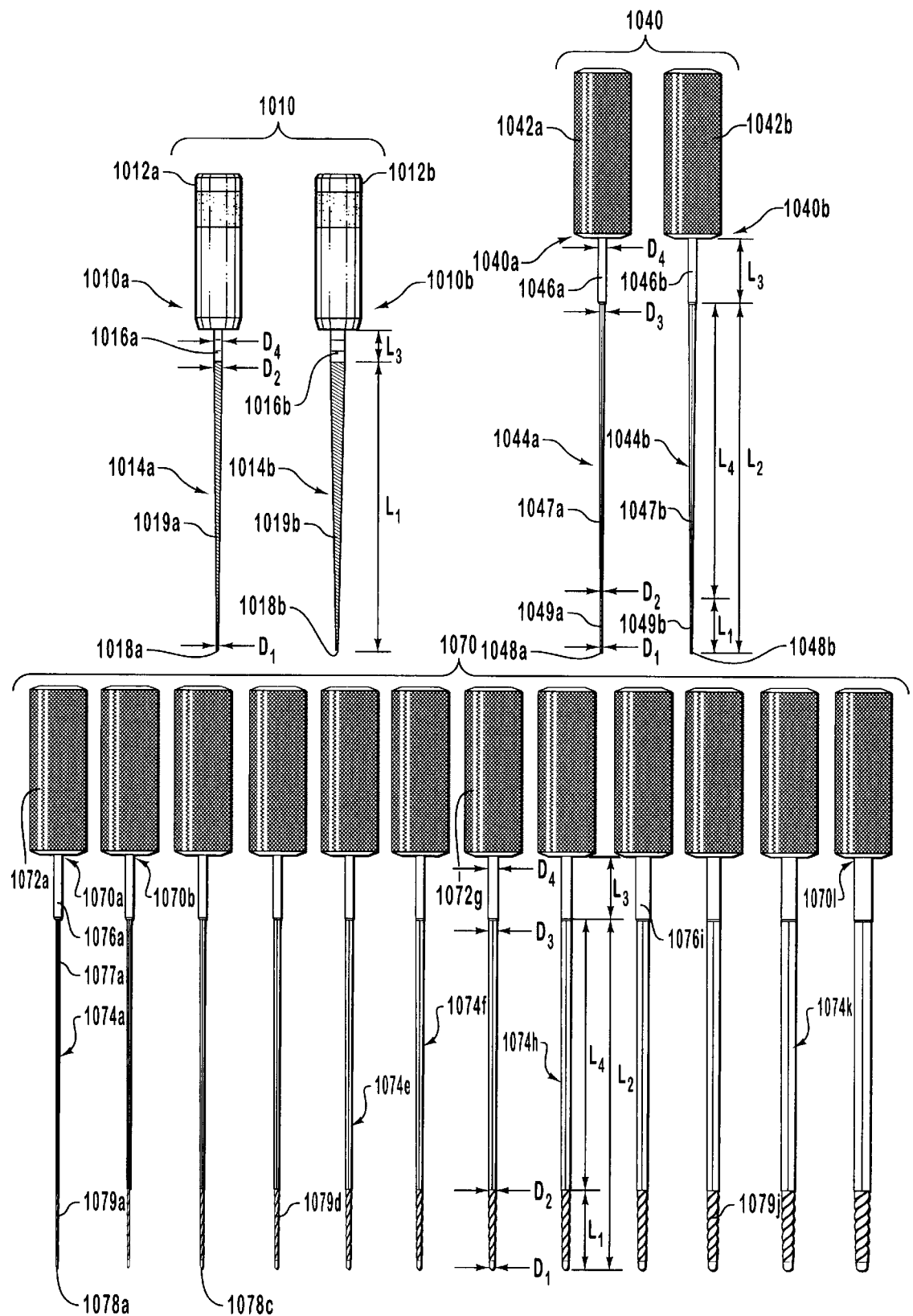
FIG. 15 is a view of a system of endodontic tools including a first set of instruments for cleaning the operative middle portion of an operative root canal, a second set of instruments for improving the access into the apical root portion and a third set of instruments for cleaning the apical root portion.

FIG. 15 depicts three sets of instruments identified at 1010, 1040 and 1070 which are used to prepare a root canal. The sets of instruments identified respectively at 1010, 1040 and 1070 are respectively used to clean the operative middle portion, to improve access into the apical portion and to clean the apical root portion. As shown, instruments 1010a and 1010b have files 1014a and 1014b. Each file has a shank portion 1016 which tapers to an abrading portion 1019 configured like conventional K-files and terminating at a tip 1018. Incrementally adjustable handles 1012a and 1012b are respectively positioned on smooth shank portions 1016a and 1016b. These handles are configured for use being held in a mated configuration by a chuck of a handpiece head. An instrument such as instrument 1010a or a set of instruments such as 1010a and 1010b comprises a first endodontic instrument means for anatomically removing and anatomically cleaning essentially all pulp material from the operative middle portion without significantly removing pulp material from the apical root portion.

As indicated above, the apical root portion of the root canal can be cleaned shown after removing and cleaning essentially all pulp material from the operative middle portion of an operative root canal in conformance with the anatomical shape of the operative middle portion by flexibly moving an instrument within the operative middle portion. However, it is preferable to improve the access into the apical root portion before cleaning the apical root portion of the root canal.

As shown in FIG. 15, the handles of the instruments used to improve the access into the apical root portion or to clean the apical root portion are not configured with an incrementally adjustable handle such as handles 1012a–b as these steps are preferably manually achieved. While the shape of these handles as well as those of the instruments 1070 enable them to be held in a mated configuration by chuck 700 if necessary, it is generally adequate to merely manually rotate the file within the apical root portion and/or move the file in a longitudinal motion. More specifically, after the file reaches the apex or approximately reaches the apex, the file is preferably moved upward while simultaneously being rotated, and it is withdrawn in order to be cleaned before being reintroduced. Although, the instruments used to improve the access into the apical portion or to clean the apical portion are not necessarily used with an incrementally adjustable handle in a handpiece, these steps are, however, briefly described herein to fully appreciate the systems and methodology.

It is beneficial to widen the tract of the root canal to provide access for thin irrigation needles into the apical root portion so as to maintain the smear layer in solution within the apical root portion, thereby avoiding smear layer accumulation. Additionally, it is useful to maintain the debris derived from cleaning the root canal in suspension to avoid filling the apical portion of the root canal with a plug. If the apical portion becomes filled, there is an increased likelihood that the progress of the instrumentation may be stopped or that debris may be pushed out of the tooth. Accordingly, by optionally widening the access to enable irrigation needles to deliver irrigants to the apical root portion, the apical root portion is more accessible to the subsequent apical cleaning instruments and the cleaning instruments are less likely to be blocked.

Thin irrigation needles typically have a diameter no smaller than about 0.30 mm so it may be necessary to increase the diameter of portions of the root canal up to about 0.35 mm or even up to about 0.40 mm, particularly within the region of the boundary between the operative middle portion and the apical root portion. Note that the diameter need only be slightly larger than a thin irrigation needle in order to provide adequate access.

While the diameters of some root canals within the region of the boundary between the operative middle portion and the apical root portion and even within the apical portion may already be large enough to enable irrigation needles to deliver irrigants as far as is necessary, it is generally necessary to widen the diameter within the apical portions or at least at the tops of the apical portions. It is not necessary for the entire apical portion to be widened up to about 0.35 mm or about 0.40 mm, just enough of the apical portion should be widened so that the irrigants can be delivered as needed. However, the length of files used to widen the apical portion is preferably sufficient to at least approximately reach the apex. Accordingly, the top of the abrading portion may be flared to enable the upper area of the apical portion to be widened up to about 0.40 mm while the tip diameter which is at or near the apex is preferably significantly smaller. Note that in addition to abrading at least the top of the apical portion, it may also be necessary to widen the diameter at the region of the base of the operative middle portion with the widening at the top of the apical portion.

The files of instruments used to optionally improve access into the apical portion and those used to clean the apical portion have similar configurations. Typically, the instruments used to improve the access into the apical portion, have the same lengths as the instruments subsequently used to clean the apical portion so that the entire apical portion is first widened and then cleaned. The lengths are preferably sufficient such that when the file is inserted into the root canal the tip can at least approximately reach the apex. Such file lengths are typically within a range from about 8 mm to about 35 mm, more typically in a range from about 14 mm to about 35 mm and most typically in a range from about 12 mm to about 33 mm.

The instruments, however, typically have different tip diameters and tapers along their respective abrading portions. The apical portion access instruments generally have much smaller tip diameters and much greater tapers than the instruments used to clean the apical portion for safe widening of apical portions. Note that before widening the apical portion of the root canal, it is preferable to make a predetermination of the desired diameter.

A file of an instrument designed for improving access to the apical root portion of a root canal or for cleaning the apical portion may be configured to abrade along its entire length; however, it preferably has an abrading portion from its tip part way upward towards its proximal end such that the remainder of the file is relatively smooth. More particularly, each file is preferably configured with an abrading portion along less than about half of the length of the file and more preferably about one-third of the length between its tip and top end Accordingly, the length of the abrading portion is generally within a range from about 1 mm to about 35 mm, more preferably in a range from about 2 mm to about 16 mm and most preferably in a range from about 3 mm to about 6 mm. In a preferred configuration, the abrading portion is about 5 mm or about 6 mm.

FIG. 15 depicts set 1040, used to improve access into the apical portion, as including two instruments, 1040a–b. Each file has three sections including a smooth shank portion, a square portion and an abrading portion. For example, instrument 1040a has a file 1044a with smooth shank portion 1046a, a square portion 1047a, an abrading portion 1049a and a file tip 1048a. As shown, the smooth shank portion 1046a is the top section of file 1044a and a handle 1042 is positioned on shank portion 1046a. Smooth shank portion 1046a tapers to square portion 1047a which is between shank portion 1046a and abrading portion 1049a. The taper of the files from the tip ($D_1$) to the diameter at the top of the square portion ($D_3$) remains constant. The tip diameter ($D_1$) of the instruments in this set remains constant while the diameter at the top of the cutting area or abrading portion ($D_2$), is graduated from instrument 1040a to 1040b. An instrument such as file instrument 1040a or a set of file instruments such as 1040a and 1040b comprises a second endodontic instrument means for improving access into the apical root portion after the pulp material has been essentially removed from the operative middle portion by the first endodontic instrument means.

FIG. 15 also depicts set 1070, used to clean the apical portion, as including twelve instruments, 1070a–l, which are configured similarly to instruments 1040a–b. Instruments 1070a–l have a handle 1072 opposite a file 1074. Each file 1074 has a smooth shank portion 1076a, a square portion 1077, an abrading portion 1079 and a file tip 1078. After selecting an instrument from set 1070, the practitioner then determines, based on feel and experience, whether the file is appropriately sized or whether a larger or smaller file is needed. For instance, if the practitioner selects instrument 1070b which has a tip diameter, for example of 0.15 mm, and the file binds after insertion, then the practitioner would switch to instrument 1070a which has, for example, a tip diameter of 0.10 mm. Similarly, if instrument 1070b is too loose then the practitioner would then switch to instrument 1070c which has a tip diameter of 0.20 mm The practitioner then uses that appropriately sized instrument to clean the apical portion of the root canal by hand. If the practitioner concludes after using an appropriately sized file, that further instrumentation is still needed within the apical portion then the instrument with the next largest file may be used. It is typically unnecessary to use a third instrument with an even larger file after using a series of two instruments. However, the practitioner may clean the apical root portion with a series of more than two instruments as deemed necessary by the practitioner in order to fully clean the apical portion.

A file instrument such as file instrument 1070a or a set of file instruments such as 1070a–l are examples of third endodontic instrument means for optionally, abrasively cleaning and removing essentially all remaining pulp material from the apical root portion after the pulp material has been essentially removed from the operative middle portion. The apical root portion may also be cleaned by merely delivering an irrigant from a conventional endodontic irrigation needle after the operative middle portion has been cleaned. Such an endodontic irrigation needle is an example of means for cleaning the apical root portion, after the pulp material has been essentially removed from the operative middle portion, by delivering an irrigant into the apical portion. The means for cleaning the apical root portion by delivering an irrigant into the apical root portion and the third endodontic instrument means are both examples of means for cleaning the apical root portion after the pulp material has been essentially removed from the operative middle portion. All of the sets of instruments used in this methodology may be sold together as a comprehensive kit or various sets may be grouped together as kits intended for use with teeth of particular lengths.

The present invention provides many benefits and advantages. The dental instrument of the invention allows a single instrument to be used to clean root canals having varying lengths. The present invention also provides for accurate, reliable, and quick adjustment of the working length thereof as used with an appropriate endodontic handpiece. Once set, the working length remains the same throughout an endodontic procedure such as root canal therapy. The handpiece also has a rim which provides an effective stop. These features are particularly advantageous when used to clean the operative middle portion of a root canal being cleaned in the phases described above.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for abrading root canal surfaces, comprising:
   identifying an operative length of a root canal,
   obtaining an endodontic instrument comprising
      a file adapted to remove and clean pulp material from a root canal during an endodontic procedure in an abrasive action, the file having a proximal end and a distal insertion end, and
      a handle having a top end and a bottom end and a diameter that is greater than the diameter of the proximal end of the file, the proximal end of the file being substantially concentric with the handle and extending from the bottom end of the handle;
   obtaining an endodontic handpiece head adapted to receive the handle and releasably hold the handle while rotating the endodontic instrument;
   inserting the handle of the endodontic instrument into the endodontic handpiece head;
   adjusting the position of the handle within the endodontic handpiece head such that the instrument has a desired working length relative to the endodontic handpiece head;
   securing the handle within the endodontic handpiece head through pressure applied by the endodontic handpiece head against the handle;
   inserting the file into the root canal; and
   urging the file against surfaces in the root canal as the instrument is operatively moved by the endodontic handpiece head.

2. The method as defined in claim 1, wherein the handle has a uniform diameter and cross-sectional shape along most of its length.

3. The method as defined in claim 1, wherein the handle is secured within the endodontic handpiece head in a mated latchless configuration.

4. The method as defined in claim 1, wherein the handle has a uniform diameter and cross-sectional shape along most of its length, and wherein the handle is secured within the endodontic handpiece head in a mated latchless configuration.

5. The method as defined in claim 1, wherein the handle has a peanut shape.

6. The method as defined in claim 1, wherein the handle includes means for visually identifying the length of the file.

7. The method as defined in claim 1, wherein the instrument includes at least one incremental adjustment indicator adapted to indicate the working length of the instrument relative to the endodontic handpiece head.

8. The method as defined in claim 1, wherein the handle includes at least one incremental adjustment indicator adapted to indicate the working length of the instrument relative to the endodontic handpiece head.

9. The method as defined in claim 1, wherein the file means includes at least one incremental adjustment indicator adapted to indicate the working length of the instrument relative to the endodontic handpiece head.

10. The method as defined in claim 1, wherein the instrument includes a uniform incremental adjustment indicator adapted to uniformly the working length of the instrument relative to the endodontic handpiece head.

11. The method as defined in claim 1, wherein the instrument includes markings spaced in increments and located to indicate the working length of the instrument relative to the endodontic handpiece head.

12. The method as defined in claim 1, wherein the instrument has distinct sections that each have a particular incremental length and wherein the sections are located to indicate the working length of the instrument relative to the endodontic handpiece head.

13. The method as defined in claim 1, wherein the method includes measuring the working length of the instrument.

14. The method as defined in claim 1, further including using the endodontic handpiece head as a stop to prevent the endodontic instrument from being inserted into the root canal beyond its working length.

15. The method as defined in claim 1, wherein the endodontic handpiece head has a rim that is adapted for resting on the coronal surface of a tooth to act as a stop during an endodontic procedure.

16. The method as defined in claim 1, wherein the endodontic handpiece head has a rim that is essentially coplanar with any bottom surfaces of the endodontic handpiece head.

17. A method for abrading root canal surfaces, comprising:
    identifying an operative length of an operative root canal,
    obtaining an endodontic instrument including
        file means for removing and cleaning pulp material from a root canal during an endodontic procedure in an abrasive action, the file means having a proximal end and a distal insertion end,
        handle means for operatively moving the file means to facilitate an endodontic procedure, the handle means having a top end and a bottom end, the file means extending from the bottom end of the handle means, and
        incremental adjustment indicator means, disposed on at least one of the file means or the handle means, for indicating the working length of the instrument;
    obtaining an endodontic handpiece head means for receiving the handle means and for releasably holding the handle means while rotating the endodontic instrument;
    inserting the handle means of the endodontic instrument into the endodontic handpiece head means;
    adjusting the position of the handle means within the endodontic handpiece head means by referencing the incremental adjustment indicator means relative to the endodontic handpiece head means such that such that the instrument has a desired working length;
    securing the handle means within the endodontic handpiece head means through pressure applied by the endodontic handpiece head means against the handle means;
    inserting the file means into the operative root canal; and
    urging the file means against surfaces in the operative root canal as the instrument is operatively moved by the endodontic handpiece head means.

18. In a system that includes an endodontic handpiece having a chuck, an improved endodontic instrument which can be secured within the chuck when using the instrument to perform endodontic procedures such as root canal therapy, the improved instrument comprising:
    file means for producing an abrasive action for purposes of removing and cleaning pulp material from a root canal during an endodontic procedure,
        wherein the file means has a proximal end opposite a distal insertion end,
        wherein the file means has an abrading portion along most of its length and a shank portion at its proximal end,
    handle means for operatively moving the file means to facilitate an endodontic procedure,
        wherein the handle means has a top end opposite from a bottom end,
        wherein the handle means is integral and fixedly attached to the file means to enable the file means to be operatively moved during an endodontic procedure as the handle means is rotated by an endodontic handpiece,
        wherein the handle means has a length and configuration that enables the handle means to be recessed and held within a chuck of an endodontic handpiece head in a latchless configuration through pressure exerted by the endodontic handpiece head whereby the working length of the instrument can be varied based on the position of the handle means within the chuck of the endodontic handpiece head, and
        wherein the shank portion of the file means includes incremental adjustment indicator means for indicating the desired working length of the instrument once the handle means is held within the chuck of the endodontic handpiece head based on the position of the incremental adjustment indicator means relative to the chuck of the endodontic handpiece head such that the working length of the instrument can be easily determined by viewing the incremental adjustment indicator means.

19. The instrument as defined in claim 18, wherein the top end of the handle means is cylindrical.

20. The instrument as defined in claim 18, wherein the length of the handle means is less than 12 mm.

21. The instrument as defined in claim 18, wherein the length of the handle means is less than about 10 mm such that the handle means can be moved as desired within the chuck and then to be securely held and still be flush or recessed relative to a rim of the handpiece.

22. The instrument as defined in claim 18, wherein the handle means has a uniform diameter and cross-sectional shape along most of its length.

23. The instrument as defined in claim 18, wherein the handle means has a uniform diameter and cross-sectional shape along its entire length.

24. The instrument as defined in claim 18, wherein the handle means has a peanut shape.

25. The instrument as defined in claim 18, wherein the handle means includes means for visually identifying the length of the file means.

26. The instrument as defined in claim 18, wherein the incremental adjustment indicator means includes uniform incremental adjustment indicator means for uniformly indicating the working length of the instrument relative to the endodontic handpiece head means.

27. The instrument as defined in claim 18, wherein the incremental adjustment indicator means includes gradient markings spaced in increments.

28. In a system that includes an endodontic handpiece having a chuck, an improved endodontic instrument which can be recessably secured within the chuck when using the instrument to perform endodontic procedures such as root canal therapy, the improved instrument comprising:
   a file having an abrading portion configured to remove and clean pulp material from a root canal during an endodontic procedure in an abrasive action,
      wherein the file has a proximal end opposite from a distal insertion end which terminates at a tip,
      wherein the file has an abrading portion along most of its length and a shank portion at its proximal end,
   a handle having a top end opposite from a bottom end,
      wherein the handle is integral and fixedly attached to the file to enable the file to be operatively moved during an endodontic procedure as the handle is rotated by an endodontic handpiece,
      wherein the handle has a length and configuration that enables the handle to be recessed and held within a chuck of an endodontic handpiece head in a latchless configuration through pressure exerted by the endodontic handpiece head whereby the working length of the instrument can be varied based on the position of the handle within the chuck of the endodontic handpiece head, and
      wherein the shank portion of the file includes incremental adjustment indicators which indicate the working length of the instrument once the handle is held within the chuck of the endodontic handpiece head based on the position of the incremental adjustment indicators relative to the chuck of the endodontic handpiece head such that the working length of the instrument can be easily determined by viewing the incremental adjustment indicators.

29. The instrument as defined in claim 28, wherein the top end of the handle is cylindrical.

30. The instrument as defined in claim 28, wherein the length of the handle is less than 12 mm.

31. The instrument as defined in claim 28, wherein the length of the handle is less than about 10 mm such that the handle can be moved as desired within the chuck and then to be securely held and still be flush or recessed relative to a rim of the handpiece.

32. The instrument as defined in claim 28, wherein the handle has a uniform diameter and cross-sectional shape along most of its length.

33. The instrument as defined in claim 28, wherein the handle has a uniform diameter and cross-sectional shape along its entire length.

34. The instrument as defined in claim 28, wherein the handle has a peanut shape.

35. The instrument as defined in claim 28, wherein the handle includes means for visually identifying the length of the file.

36. The instrument as defined in claim 28, wherein the incremental adjustment indicators includes uniform incremental adjustment indicators configured to uniformly indicate the working length of the instrument relative to the endodontic handpiece head.

37. A method for abrading root canal surfaces, comprising:
   identifying an operative length of an operative root canal,
   obtaining an endodontic instrument including
      a file adapted to remove and clean pulp material from a root canal during an endodontic procedure in an abrasive action, the file having a proximal end and a distal insertion end, and
      a handle having a top end and a bottom end and a diameter that is greater than the diameter of the proximal end of the file, the proximal end of the file extending from the bottom end of the handle;
   obtaining a powered endodontic handpiece having a head adapted to receive the handle and releasably hold the handle while rotating the endodontic instrument;
   inserting the handle of the endodontic instrument into the head of the endodontic handpiece;
   adjusting the position of the handle within the head of the endodontic handpiece such that the endodontic instrument has a desired working length relative to the head of the endodontic handpiece;
   securing the handle within the head of the endodontic handpiece through pressure applied by the head against the handle;
   inserting the file into the root canal; and
   urging the file against surfaces in the operative root canal as the instrument is operatively moved by the head of the endodontic handpiece.

* * * * *

UNITED STATES PATENT AND TRADEMARK OFFICE
CERTIFICATE OF CORRECTION

PATENT NO. : 6,575,747 B1
DATED : June 10, 2003
INVENTOR(S) : Francesco Riitano and Dan E. Fischer It is certified that error appears in the above-identified patent and that said Letters Patent is hereby corrected as shown below:

Column 1,
Line 38, after "end" insert -- . --

Column 4,
Line 55, change "rated" to -- mated --

Column 5,
Line 19, after "possible" insert -- to --

Column 6,
Lines 38 & 42, after "is" insert -- a --
Line 49, change "users" to -- user's --

Column 9,
Line 1, after "nickel/titanium" insert -- . --
Line 53, change "2 mm" to -- 2 mm. --

Column 10,
Line 3, change "extend" to -- extends --
Line 7, change "instruments" to -- instrument --
Lines 54-55, change "preferably" to -- preferable --

Column 11,
Line 23, change "mm" to -- mm. --
Line 27, change "provides" to -- provide --
Line 47, change "instruments" to -- instrument --

Column 12,
Line 31, after "it" insert -- is --

Column 13,
Line 44, delete "a"

Column 15,
Line 6, after "may" insert -- be --
Line 18, change "9 mm" to -- 9 mm. --
Line 33, change "10" to -- 110 --

UNITED STATES PATENT AND TRADEMARK OFFICE
CERTIFICATE OF CORRECTION

PATENT NO.    : 6,575,747 B1
DATED         : June 10, 2003
INVENTOR(S)   : Francesco Riitano and Dan E. Fischer It is certified that error appears in the above-identified patent and that said Letters Patent is hereby corrected as shown below:

<u>Column 23,</u>
Line 37, change "files" to -- file --

<u>Column 26,</u>
Line 60, after "compared" insert -- to --

<u>Column 28,</u>
Line 19, change "mm," to -- mm; --
Line 62, after "end" insert -- . --

<u>Column 29,</u>
Line 38, change "0.20 mm" to -- 0.20 mm. --

<u>Column 31,</u>
Line 17, after "uniformly" insert -- indicate --
Line 66, delete the second occurrence of "such that"

Signed and Sealed this

Sixth Day of January, 2004

JAMES E. ROGAN
*Director of the United States Patent and Trademark Office*